US009140635B2

(12) United States Patent
Graham et al.

(10) Patent No.: US 9,140,635 B2
(45) Date of Patent: Sep. 22, 2015

(54) ASSAY FOR MEASURING ENZYMATIC MODIFICATION OF A SUBSTRATE BY A GLYCOPROTEIN HAVING ENZYMATIC ACTIVITY

(75) Inventors: Carrie Graham, Raleigh, NC (US); Allen Eckhardt, San Diego, CA (US); Lisa Perkins, Madison, WI (US)

(73) Assignee: Advanced Liquid Logic, Inc., San Diego, CA (US)

( * ) Notice: Subject to any disclaimer, the term of this patent is extended or adjusted under 35 U.S.C. 154(b) by 11 days.

(21) Appl. No.: 14/116,544

(22) PCT Filed: May 9, 2012

(86) PCT No.: PCT/US2012/037036
§ 371 (c)(1),
(2), (4) Date: Mar. 17, 2014

(87) PCT Pub. No.: WO2012/154794
PCT Pub. Date: Nov. 15, 2012

(65) Prior Publication Data
US 2015/0050664 A1 Feb. 19, 2015

Related U.S. Application Data

(60) Provisional application No. 61/484,490, filed on May 10, 2011.

(51) Int. Cl.
*G01N 33/573* (2006.01)
*G01N 1/40* (2006.01)
*C12N 9/16* (2006.01)
*C12N 9/24* (2006.01)
*C12N 9/26* (2006.01)
*C12N 9/38* (2006.01)
*G06F 19/10* (2011.01)

(52) U.S. Cl.
CPC *G01N 1/405* (2013.01); *C12N 9/16* (2013.01); *C12N 9/2402* (2013.01); *C12N 9/2408* (2013.01); *C12N 9/2471* (2013.01); *C12Y 301/06013* (2013.01); *C12Y 302/01023* (2013.01); *C12Y 302/01076* (2013.01); *G01N 33/573* (2013.01); *G01N 2333/924* (2013.01); *G01N 2333/928* (2013.01); *G01N 2333/938* (2013.01); *G01N 2800/38* (2013.01); *G06F 19/10* (2013.01)

(58) Field of Classification Search
USPC .......................................................... 356/411
See application file for complete search history.

(56) References Cited

U.S. PATENT DOCUMENTS

| 4,269,605 | A | * | 5/1981 | Dean et al. ....................... 436/67 |
| 4,636,785 | A | | 1/1987 | Le Pesant |
| 5,181,016 | A | | 1/1993 | Lee et al. |
| 5,486,337 | A | | 1/1996 | Ohkawa et al. |
| 5,859,213 | A | * | 1/1999 | Stefas et al. ................... 530/415 |
| 6,063,339 | A | | 5/2000 | Tisone et al. |
| 6,130,098 | A | | 10/2000 | Handique et al. |
| 6,294,063 | B1 | | 9/2001 | Becker et al. |
| 6,565,727 | B1 | | 5/2003 | Shenderov |
| 6,773,566 | B2 | | 8/2004 | Shenderov |
| 6,790,011 | B1 | | 9/2004 | Le Pesant et al. |
| 6,911,132 | B2 | | 6/2005 | Pamula et al. |
| 6,924,792 | B1 | | 8/2005 | Jessop |
| 6,977,033 | B2 | | 12/2005 | Becker et al. |
| 6,989,234 | B2 | | 1/2006 | Kolar et al. |
| 7,052,244 | B2 | | 5/2006 | Fouillet et al. |
| 7,163,612 | B2 | | 1/2007 | Sterling et al. |
| 7,211,223 | B2 | | 5/2007 | Fouillet et al. |
| 7,255,780 | B2 | | 8/2007 | Shenderov |
| 7,328,979 | B2 | | 2/2008 | Decre et al. |
| 7,329,545 | B2 | | 2/2008 | Pamula et al. |
| 7,439,014 | B2 | | 10/2008 | Pamula et al. |
| 7,458,661 | B2 | | 12/2008 | Kim et al. |
| 7,531,072 | B2 | | 5/2009 | Roux et al. |
| 7,547,380 | B2 | | 6/2009 | Velev |
| 7,569,129 | B2 | | 8/2009 | Pamula et al. |
| 7,641,779 | B2 | | 1/2010 | Becker et al. |
| 7,727,466 | B2 | | 6/2010 | Meathrel et al. |

(Continued)

FOREIGN PATENT DOCUMENTS

| CN | 101472940 | 7/2009 |
| EP | 0221561 | 5/1987 |

(Continued)

OTHER PUBLICATIONS

Sista R. et al. Multiplex Newborn Screening for Pompe, Fabry, Hunter, Gaucher, and Hurler Diseases Using a Digital Microfluidic Platform. Clinica Chimica Acta 424:12-18, May 7, 2013.*
Benton et al., "Library Preparation Method 1 DNA Library Construction for Illumine SBS Sequencing Platforms using NEBNext® Library Preparation Reagents", Application Note, NuGEN, 2011.
Boles et al., "Droplet-Based Pyrosequencing Using Digital Microfluidics", Analytical Chemistry, vol. 83, Sep. 2011, 8439-47.
Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.
Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-Dx-Wkshop/index.cfm, Jun. 28, 2011.

(Continued)

*Primary Examiner* — Ralph Gitomer
(74) *Attorney, Agent, or Firm* — Kajal Chowdhury; Illumina, Inc.

(57) ABSTRACT

Methods of conducting an assay for measuring enzymatic modification of a substrate by a glycoprotein having enzymatic activity are provided. The methods include concentrating the glycoprotein having enzymatic activity by capturing the glycoproteins from the input sample on a solid support, washing the glycoproteins captured on a solid support to remove unbound portions of the input sample, adding an enzyme substrate to the output sample comprising glycoproteins having enzymatic activity, and measuring enzymatic modification of the substrate. In some examples, the capturing of the glycoprotein and subsequent washing steps are performed in one or more droplets in oil.

16 Claims, 20 Drawing Sheets

(56) References Cited

U.S. PATENT DOCUMENTS

| | | |
|---|---|---|
| 7,727,723 B2 | 6/2010 | Pollack et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,317,990 B2 | 11/2012 | Pamula et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0096221 A1 | 5/2003 | Littman et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0055891 A1 | 3/2004 | Pamula et al. |
| 2004/0058450 A1 | 3/2004 | Pamula et al. |
| 2004/0231987 A1 | 11/2004 | Sterling et al. |
| 2006/0021875 A1 | 2/2006 | Griffith et al. |
| 2006/0054503 A1 | 3/2006 | Pamula et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0166224 A1* | 7/2009 | Yang et al. ............ 205/792 |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1* | 2/2010 | Pamula et al. ............ 435/18 |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |

(56) References Cited

U.S. PATENT DOCUMENTS

| | | |
|---|---|---|
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0017544 A1 | 1/2013 | Eckhardt et al. |
| 2013/0018611 A1 | 1/2013 | Sturmer |
| 2013/0059366 A1 | 3/2013 | Pollack et al. |

FOREIGN PATENT DOCUMENTS

| | | |
|---|---|---|
| EP | 0221561 A2 | 5/1987 |
| JP | 2006329899 A | 12/2006 |
| JP | 2006329904 A | 12/2006 |
| WO | 0069565 A1 | 11/2000 |
| WO | 0073655 A1 | 12/2000 |
| WO | 2004029585 A1 | 4/2004 |
| WO | 2004030820 | 4/2004 |
| WO | 2005047696 A1 | 5/2005 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007/120240 A2 | 10/2007 |
| WO | 2007120240 A2 | 10/2007 |
| WO | 2007120241 A2 | 10/2007 |
| WO | 2007123908 A2 | 11/2007 |
| WO | 2008051310 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 A1 | 4/2009 |
| WO | 2009052348 A2 | 4/2009 |
| WO | 2009076414 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010004014 A1 | 1/2010 |
| WO | 2010006166 A2 | 1/2010 |
| WO | 2010009463 A2 | 1/2010 |
| WO | 2010019782 A2 | 2/2010 |
| WO | 2010027894 A2 | 3/2010 |
| WO | 2010042637 A2 | 4/2010 |
| WO | 2010077859 A3 | 7/2010 |
| WO | 2011002957 A2 | 1/2011 |
| WO | 2011020011 A2 | 2/2011 |
| WO | 2011057197 A2 | 5/2011 |
| WO | 2011084703 A2 | 7/2011 |
| WO | 2011126892 A2 | 10/2011 |
| WO | 2012009320 A2 | 1/2012 |
| WO | 2012012090 A2 | 1/2012 |
| WO | 2012037308 A2 | 3/2012 |
| WO | 2012068055 A3 | 5/2012 |
| WO | 2013009927 A3 | 1/2013 |

OTHER PUBLICATIONS

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Cohen, "Automated Multianalyte Screening Tool for Classification of Forensic Samples", NIJ conference 2012, http://www.nij.gov/nij/events/nij_conference/2012/nij-2012-program-book.pdf, 2012.

Cohen, "Digital Microfluidic Sample Prep & Bioanalytical Systems", BioDot Workshop: From R&D to Quantitative IVDs, Irvine, CA, Apr. 24, 2012.

Cotten et al., "Digital Microfluidics: a novel platform for multiplexed detection of lysosomal storage diseases", Abstract # 3747.9. Pediatric Academic Society Conference, 2008.

Delapierre et al., "SmartDrop: An Integrated System from Sample Collection to Result using real-time PCR," 4th National Bio-Threat Conference, Dec. 7-9, 2010, New Orleans, LA, USA; Abstract in Proceedings, Poster presented at conference.

Delattre, Movie in news on TF1 (at 12'45" Cyril Delattre), http://videos.tf1.fr/jt-we/zoom-sur-grenoble-6071525.html, 2009.

Delattre, Movie in talk show "C Dans l'air" (at 24" Cyril Delattre), http://www.france5.fr/c-dans-l-air/sante/bientot-vous-ne-serez-plus-malade-31721, 2009.

Delattre, Movie on Web TV—Cite des sciences (at 3'26" Cyril Delattre), http://www.universcience.tv/video-laboratoire-de-poche-793.html, 2009.

Delattre et al., "Macro to microfluidics system for biological environmental monitoring", Biosensors and Bioelectronics, vol. 36, Issue 1, 2012, Available online, Apr. 27, 2012, 230-235.

Delattre et al., "SmartDrop: an integrated system from sample preparation to analysis using real-time PCR", 10th International Sympo-

(56) References Cited

OTHER PUBLICATIONS sium on Protection against Chemical and Biological Warfare Agents; Stockholm, Sweden; poster, Jun. 10, 2010.
Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.
Delattre et al., "Towards an industrial fabrication process for electrowetting chip using standard MEMS Technology", μTAS2008, San Diego; poster presented, Oct. 15, 2008.
Delattre et al., "Towards an industrial fabrication process for electrowetting chip using standard MEMS Technology", μTAS2008, San Diego; Abstract in proceedings, Oct. 13-16, 2008, 1696-1698.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Eckhardt et al., "Development and validation of a single-step fluorometric assay for Hunter syndrome", APHL Newborn Screening and Genetic Testing Symposium, San Diego, 2011.
Emani et al., "Novel microfluidic platform for automated lab-on-chip testing of hypercoagulability panel", Blood Coagulation and Fibrinolysis, vol. 23(8), 2012, 760-8.
Emani et al., "Novel Microfluidic Platform for Point of Care Hypercoagulability Panel Testing", Circulation, vol. 122, 2010, A14693.
Fair et al., "A Micro-Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Workshop, Rochester, NY, May 31, 2006.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, preconcentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fair, "Scaling of Digital Microfluidic Devices for Picoliter Applications", The 6th International Electrowetting Meeting, Aug. 20-22, 2008, p. 14.
Fouillet, "Bio-Protocol Integration in Digital Microfluidic Chips", The 6th International Electrowetting Meeting, Aug. 20-22, 2008, p. 15.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Fouillet et al., "Digital microfluidic design and optimization of classic and new fluidic functions for lab on a chip systems", Microfluid Nanofluid, vol. 4, 2008, 159-165.

Graham et al., "Development of Quality Control Spots for Lysosomal Storage Disorders under cGMP", APHL Newborn Screening and Genetic Testing Symposium, San Diego, 2011.
Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.
Hua et al., "Rapid Detection of Methicillin-Resistant *Staphylococcus aureus* (MRSA) Using Digital Microfluidics", 12th Intl Conference on Miniaturized Systems for Chemistry and Life Sciences, Proc. μTAS, Oct. 12-16, 2008.
Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.
Jary et al., "SmartDrop, Microfluidics for Biology", Forum 4i 2009, Grenoble, France; Flyer distributed at booth, May 14, 2009.
Jinks et al., "Newborn Screening for Krabbe and other Lysosomal Storage Diseases", The 3rd Annual Workshop on Krabbe Disease, Java Center, New York, Jul. 19-21, 2010.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.
Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.
Kleinert, "Electric-Field-Assisted Convective Assembly of Colloidal Crystal Coatings", Langmuir, vol. 26(12), May 13, 2010, 10380-10385.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.
Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal
&id=ASMECP002010054501000023900000, Aug. 1-5, 2010.
Marchand et al., "Organic Synthesis in Soft Wall-Free Microreactors: Real-Time Monitoring of Fluorogenic Reactions", Analytical Chemistry, vol. 80, Jul. 2, 2008, 6051-6055.
Millington et al., "Applications of tandem mass spectrometry and microfluidics in newborn screening", Southeastern Regional Meeting of the American Chemical Society, Raleigh, North Carolina, 2012.
Millington et al., "Digital microfluidics: a future technology in the newborn screening laboratory", Seminars in Perinatology, vol. 34, Apr. 2010, 163-169.

(56) References Cited

OTHER PUBLICATIONS

Millington et al., "Digital Microfluidics: a novel platform for multiplexed detection of LSDs with potential for newborn screening", Association of Public Health Laboratories Annual Conference, San Antonio, TX, Nov. 4, 2008.
Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supt. 1), 2009, 21-33.
Paik et al., "A digital-microfluidic approach to chip cooling", IEEE Design & Test of Computers, vol. 25, Jul. 2008, 372-381.
Paik et al., "Adaptive Cooling of Integrated Circuits Using Digital Microfluidics", IEEE Transactions on VLSI, vol. 16, No. 4, 2008, 432-443.
Paik et al., "Adaptive Cooling of Integrated Circuits Using Digital Microfluidics", accepted for publication in IEEE Transactions on VLSI Systems, 2007, and Artech House, Norwood, MA, 2007.
Paik, "Adaptive Hot-Spot Cooling of Integrated Circuits Using Digital Microfluidics", Dissertation, Dept. Of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (Therminic), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik et al., "Programmable flow-through real-time PCR using digital microfluidics", Proc. Micro Total Analysis Systems (µTAS), Handout, 2007.
Paik et al., "Programmable flow-through real-time PCR using digital microfluidics", Proc. Micro Total Analysis Systems (µTAS), Poster, 2007.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula, "Digital microfluidic lab-on-a-chip for multiplexing tests in newborn screening", Newborn Screening Summit: Envisioning a Future for Newborn Screening, Bethesda, MD, Dec. 7, 2009.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.
Pamula et al., "Digital Microfluidic Platform for Multiplexing LSD Assays in Newborn Screening", LSD World Meeting, Las Vegas, NV, Feb. 16-18, 2011.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al., "Rapid LSD assays on a multiplex digital microfluidic platform for newborn screening", Lysosomal Disease Network World Symposium 2012, San Diego, CA, Feb. 8-19, 2012, 39.
Pamula, "Sample Preparation and Processing using Magnetic Beads on a Digital Microfluidic Platform", CHI's Genomic Sample Prep, San Francisco, CA, Jun. 9-10, 2009.
Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.
Pollack et al., "Applications of Electrowetting-Based Digital Microfluidics in Clinical Diagnostics", Expert Rev. Mol. Diagn., vol. 11(4), 2011, 393-407.
Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Punnamaraju, "Voltage and Photo Induced Effects in Droplet-Interface-Bilayer Lipid", PhD Thesis, University of Cincinnati, 2011.
Punnamaraju et al., "Voltage Control of Droplet Interface Bilayer Lipid Membrane Dimensions", Langmuir The ACS Journal of Surfaces and Colloids, vol. 27, Issue 2, 2011, Published on Web, Dec. 10, 2010, 618-626.
Ren et al., "Automated electrowetting-based droplet dispensing with good reproducibility", Proc. Micro Total Analysis Systems (mTAS), 7th Int. Conf. on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.

(56) References Cited

OTHER PUBLICATIONS

Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.
Rival et al., "Expression de gènes de quelques cellules sur puce EWOD/Gene expression of few cells on EWOD chip", iRTSV,http://www-dsv.cea.fr/var/plain/storage/original/media/File/iRTSV/thema_08(2).pdf (english translation), Winter 2009-2010.
Rival et al., "New insight on droplet dynamics under electrowetting actuation and design tools for speeding up product development", 8th Electrowetting Workshop, Athens, Greece. Abstract, 2012.
Rival et al., "New insight on droplet dynamics under electrowetting actuation and design tools for speeding up product development", 8th Electrowetting Workshop, Athens, Greece, Presentation, 2012.
Rival et al., "Towards Single Cells Gene Expression on EWOD Lab On Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.
Rival et al., "Towards single cells gene expression preparation and analysis on ewod lab on chip", Lab On Chip Europe 2009, Abstract in proceedings, May 19-20, 2009.
Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.
Schell et al., "Evaluation of a Digital Microfluidic real-time PCR Platform to detect DNA of Candida albicans", Eur. J. Clin Microbiol Infect Dis, Published on-line DOI 10.1007/s10096-012-15616, Feb. 2012.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Shi et al., "Evaluation of stability of fluorometric reagent kits for screening of Lysosomal Storage Disorders", APHL Newborn Screening and Genetic Testing Symposium, San Diego, 2011.
Sista et al., "96-Immunoassay Digital Microfluidic Multiwell Plate", Proc. µTAS, Oct. 12-16, 2008.
Sista, "Development of a Digital Microfluidic Lab-on-a-Chip for Automated Immunoassays with Magnetically Responsive Beads", PhD Thesis, Department of Chemical Engineering, Florida State University, 2007.
Sista et al., "Development of a digital microfluidic platform for point of care testing", Lab on a chip, vol. 8, Dec. 2008, First published as an Advance Article on the web, Nov. 5, 2008, 2091-2104.
Sista et al., "Digital Microfluidic Platform for Multiplexing Enzyme Assays: Implications for Lysosomal Storage Disease Screening in Newborns", Clinical Chemistry, vol. 57, Aug. 22, 2011, 1444-51.
Sista et al., "Digital Microfluidic platform for multiplexing LSD assays in newborn screening", APHL Newborn Screening and Genetic Testing Symposium, Orlando, May 3-6, 2010.
Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.
Sista et al., "Multiplex Digital Microfluidic Platform for Rapid Newborn Screening of Lysosomal Storage Disorders", ACMG Annual Meeting, Charlotte, NC, 2012.
Sista et al., "Performance of a digital microfluidic assay for Gaucher and Hurler disorders", APHL Newborn Screening and Genetic Testing Symposium, San Diego, 2011.
Sista et al., "Rapid, Single-Step Assay for Hunter Syndrome in Dried Blood Spots Using Digital Microfluidics", Clinica Chimica Acta, vol. 412, 2011, 1895-97.
Sista et al., "Spatial multiplexing of immunoassays for small-volume samples", 10th PI Meeting IMAT, Bethesda, 2009.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "An integrated digital microfluidic lab-on-a-chip for clinical diagnostics on human physiological fluids", Lab on a Chip, vol. 4, 2004, 310-315.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Digital Microfluidic Lab-on-a-Chip for Protein Crystallization", The 82nd ACS Colloid and Surface Science Symposium, 2008.
Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.
Srinivasan et al., "Droplet-based microfluidic lab-on-a-chip for glucose detection", Analytica Chimica Acta, vol. 507, No. 1, 2004, 145-150.
Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.
Srinivasan et al., "Feasibility of a point of care newborn screening platform for hyperbilirubinemia", APHL Newborn Screening and Genetic Testing Symposium, San Diego, 2011.
Srinivasan et al., "Low cost digital microfluidic platform for protein crystallization", Enabling Technologies for Structural Biology, NIGMS Workshop, Bethesda, MD., Mar. 4-6, 2009, J-23.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (Date) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, May 2004, 3229-3235.
Thwar et al., "DNA sequencing using digital microfluidics", Poster 42, 41st AACC's Annual Oak Ridge Conference Abstracts, Clinical Chemistry vol. 55, 2009, 1891.
Tolun et al., "A Novel Fluorometric Enzyme Analysis Method for Hunter Syndrome Using Dried Blood Spots", Mol. Genet. Metab., 105, Issue 3, 2012; doi:10.1016/j.ymgme.2011.12.011, Epub, Dec. 21, 2011, 519-521.

(56) References Cited

OTHER PUBLICATIONS

Tolun et al., "Dried blood spot based enzyme assays for lysosomal storage disorders", 2011 Tokyo Meeting on Lysosomal Storage Disease Screening, Tokyo, Aug. 5, 2011.

Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.

Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Defect-Tolerant Design and Optimization of a Digital Microfluidic Biochip for Protein Crystallization", IEEE Transactions on Computer Aided Design, vol. 29, No. 4, 2010, 552-565.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, LISA, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", Codes, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yang et al., "Manipulation of droplets in microfluidic systems", Trends in Analytical Chemistry, vol. 29, Feb. 2010, 141-157.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16., Oct. 2006, 2053-2059.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. On Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation by Traveling-Wave Dielectrophoresis (twDEP) for Digital Microfluidics", J. Microelectromechanical Systems, vol. 16, No. 6, Dec. 2007, 1472-1481.

Zhao et al., "Synchronization of Concurrently-Implemented Fluidic Operations in Pin-Constrained Digital Microfluidic Biochips", VLSI Design, (Best Paper Award), 2010.

Sparbier et al., "Analysis of Glycoproteins in Human Serum by Means of Glycospecific Magnetic Bead Separation and LC-MALDI-TOF /TOF Analysis with Automated Glycopeptide Detection", J. Biom. Tech. 2007, 18:252-258.

Watanabe et al., " Partial purification and properties of acid sphingomyelinase from rat liver", J. Lip. Research, 1983, vol. 24, 596-603.

International Search Report dated Nov. 29, 2012 from PCT International Application No. PCT/US2012/037036.

European Search Report and Opinion dated Jan. 5, 2015 from European Application No. 12781874.8.

Weaver, "Application of Magnetic Microspheres for Pyrosequencing on a Digital Microfluidic Platform", Department of Electrical and Computer Engineering, Duke University, 2005.

EP Search Report in Application No. 12781874.8 mailed Jan. 5, 2015.

Balasubramanian, et al., "The use of concanavalin A in the purification or separation of multiple forms of brain hydrolases", J. Biosci, vol. 5, 1983, 61-64.

He, et al., "Purification and Characterization of Recombinant, Human Acid Ceramidase", The Journal of Biological Chemistry, 278 (35), 2003, 32978-32986.

Sparbier, et al., "Analysis of glycoproteins in human serum by means of glycospecific magnetic bead separation and LC-MALDI-TOF/ TOF analysis with automated glycopeptide detection", Journal of biomolecular techniques: JBT, www.ncbi.nlm.nih.gov/pubmed/ 17916798, 2007, 252-258.

Watanabe, et al., "Partial purification and properties of acid spingomyelinase from rat liver", Journal of Lipid Research, http:// www.jlr.org/cgi/content/abstract/24/5/596.

Woodward, et al., "Affinity Chromatography of Beta-Glucosidase and Endo-Beta-Glucanase from Aspergillus niger on Concanavalin A-Sepharose: Implications for Cellulase Component Purification and Immobilization", Preparative Biochemistry, 16(4), 1986, 337-352.

\* cited by examiner

NSC 120634

1200

1250

ASSAY FOR MEASURING ENZYMATIC MODIFICATION OF A SUBSTRATE BY A GLYCOPROTEIN HAVING ENZYMATIC ACTIVITY

1 RELATED APPLICATIONS

This application is a 35 U.S.C. 371 U.S. national phase entry of International Application No. PCT/US2012/037036 having an international filing date of May 9, 2012, which claims the benefit of U.S. Provisional Application No. 61/484,490, filed May 10, 2011, the content of each of the aforementioned applications is herein incorporated by reference in its entirety.

2 FIELD OF THE INVENTION

The invention relates to methods of concentrating enzymes and to the use of concentrated enzymes in enzymatic assays.

3 BACKGROUND

A droplet actuator typically includes one or more substrates configured to form a surface or gap for conducting droplet operations. The one or more substrates establish a droplet operations surface or gap for conducting droplet operations and may also include electrodes arrange to conduct the droplet operations. The droplet operations substrate or the gap between the substrates may be coated or filled with a filler fluid that is immiscible with the liquid that forms the droplets.

Droplet actuators are used in a variety of applications, including molecular diagnostic assays such as enzymatic assays and immunoassays. In one application, enzymatic assays and immunoassays are used as part of a routine testing process to test newborn infants for various genetic disorders. For example, enzymatic assays may be used to test for various lysosomal storage diseases (LSD). Many genetic disorders targeted in newborn testing programs are associated with deficiencies in glycoprotein molecules (e.g., lysosomal enzymes) that may represent only a small fraction of total macromolecules in a complex biological sample, such as blood. Samples for newborn testing are typically collected by pricking the heel of the newborn to obtain a small quantity of blood (typically, two to three drops) to fill a few circles on a filter paper card. Specimens are punched from the DBS sample (i.e., one punch for each test to be performed using current technologies) and manipulated according to a specific assay protocol. Because the blood samples are spotted onto a solid medium and dried, they must be reconstituted before analysis, a step that requires dilution of the sample into a suitable liquid medium. There is a need for improved methods for increasing sensitivity of detection of target glycoprotein molecules in NBS assays.

4 BRIEF DESCRIPTION OF THE INVENTION

A method of preparing a sample for conducting an assay, the method including: providing an input sample including glycoproteins; capturing glycoproteins from the input sample on a solid support; and washing the sample support to remove unbound portions of the input sample. In certain embodiments, the method includes eluting glycoproteins form the solid support to yield an output sample. In certain embodiments, the method steps are performed in one or more droplets in oil. In certain embodiments, the eluting is accomplished by contacting the solid support with one or more glycomimetics. In certain embodiments, the eluting is accomplished by cleaving a cleavable bond between the solid support and captured glycoproteins. In certain embodiments, the input sample comprises a sample substance selected from the group consisting of: blood, plasma, serum, tears, saliva, and urine. In certain embodiments, the input sample comprises fresh blood. In certain embodiments, the input sample comprises reconstituted dried blood. In certain embodiments, the input sample consists essentially of plasma. In certain embodiments, the input sample comprises a human clinical sample. In certain embodiments, the solid support comprises concanavalin A. In certain embodiments, the solid support comprises a magnetically responsive bead. In certain embodiments, the captured glycoproteins comprise one or more enzymes. In certain embodiments, the captured glycoproteins comprise one or more glycosidase enzymes.

The invention also provides a method of conducting an assay, including: performing the enzyme concentration methods, exposing the solid support to a substrate and measuring enzymatic modification of the substrate. In certain embodiments, the enzyme is eluted or otherwise separated from the solid support prior to adding an enzyme substrate to the output sample and measuring enzymatic modification of the substrate. Typically, modification of the substrate correlates with the presence of, and/or activity of, an enzyme potentially present in the output sample. In certain embodiments, the enzyme is a lysosomal enzyme. In certain embodiments, the enzyme is a glycosylated enzyme. In certain embodiments, the method is performed at a point of sample collection. In certain embodiments, the substrate comprises a glycoside substrate. In certain embodiments, the substrate releases a detectable upon contact with the enzyme of interest. In certain embodiments, the substrate comprises a glycoside substrate which releases a fluorophore upon contact with the enzyme of interest. In certain embodiments, the substrate comprises a glycoside substrate. In certain embodiments, the point of sample collection is in the presence of the subject. In certain embodiments, the input sample is collected from a subject and immediately loaded onto a droplet actuator and the method is immediately performed.

The invention also provides a computer readable medium programmed to cause a droplet actuator to perform any of the method steps. A system including a droplet actuator coupled to and controlled by a computer programmed to cause the droplet actuator to perform any of the method steps of the methods.

5 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current. Any suitable voltage may be used. For example, an electrode may be activated using a voltage which is greater than about 150 V, or greater than about 200 V, or greater than about 250 V, or from about 275 V to about 375 V, or about 300 V. Where alternating current is used, any suitable frequency may be employed. For example, an electrode may be activated using alternating current having a frequency from about 1 Hz to about 100 Hz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a fluid path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based applications," published on Jul. 20, 2006; the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim and/or Shah et al., U.S. patent application Ser. No. 10/343,261, entitled "Electrowetting-driven Micropumping," filed on Jan. 27, 2003, Ser. No. 11/275,668, entitled "Method and Apparatus for Promoting the Complete Transfer of Liquid Drops from a Nozzle," filed on Jan. 23, 2006, Ser. No. 11/460,188, entitled "Small Object Moving on Printed Circuit Board," filed on Jan. 23, 2006, Ser. No. 12/465,935, entitled "Method for Using Magnetic Particles in Droplet Microfluidics," filed on May 14, 2009, and Ser. No. 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," *Lab Chip*, 10:832-836 (2010); the entire disclosures of which are incorporated herein by reference, along with their priority documents. Certain droplet actuators will include one or more substrates arranged with a gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the invention. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be from about 5 µm to about 600 µm, or about 100 µm to about 400 µm, or about 200 µm to about 350 µm, or about 250 µm to about 300 µm, or about 275 µm. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the invention include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the invention. Similarly, one or more of the foregoing may be used to deliver liquid into a droplet operations gap, e.g., from a reservoir in another device or from an external reservoir of the droplet actuator (e.g., a reservoir associated with a droplet actuator substrate and a fluid path from the reservoir into the droplet operations gap). Droplet operations surfaces of certain droplet actuators of the invention may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc) and NOVEC™ electronic coatings (available from 3M Company, St. Paul, Minn.), and other fluorinated monomers for plasma-enhanced chemical vapor deposition (PECVD). In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrene-sulfonate) (PEDOT:PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness in the range of about 20 to about 200 nm, preferably about 50 to about 150 nm, or about 75 to about 125 nm, or about 100 nm. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass) and PARYLENE™ N (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the invention may derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, and other fluorinated monomers for plasma-enhanced chemical vapor deposition (PECVD). Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the invention includes those described in Meathrel, et al., U.S. Pat. No. 7,727,466, entitled "Disintegratable films for diagnostic devices," granted on Jun. 1, 2010.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the gap of a droplet actuator is typically filled with a filler fluid. The filler fluid may, for example, be a low-viscosity oil, such as silicone oil or hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the invention are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Reservoir" means an enclosure or partial enclosure configured for holding, storing, or supplying liquid. A droplet actuator system of the invention may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or fluid path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the invention, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

6 BRIEF DESCRIPTION OF THE DRAWINGS

7 DESCRIPTION

Figure 1:
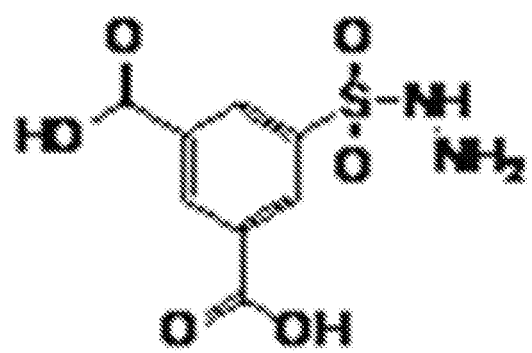
FIG. 1 shows an example of a glycomimetic (NSC 120634) that is an effective inhibitor (competitor) of ConA-carbohydrate binding.

The present invention provides methods to concentrate glycoproteins (e.g., enzymes) in a biological sample for newborn testing for metabolic disorders. In various embodiments, concanavalin A (ConA) immobilized on a solid support may be used to concentrate N-glycosylated proteins (e.g., enzymes) in a biological sample prior to performing one or more newborn screening assays (e.g., enzymatic assays). In one embodiment, samples for newborn testing for metabolic disorders may be prepared using on-bench glycoprotein concentration protocols prior to loading on a droplet actuator. In another embodiment, concentration of glycoproteins in a biological sample may be performed directly on a droplet actuator. In various embodiments, the invention includes methods for concentrating enzymatic activity in biological samples, such as fresh blood and/or plasma samples and dried blood and/or plasma samples. The methods of the invention substantially reduce contaminants (e.g., assay inhibitors) and increase target protein (e.g., enzyme) concentration in a biological sample. The methods of the invention provide improved sensitivity in newborn screening assays (e.g., enzymatic assays) and other diagnostic tests.

In one example, the methods of the invention may be used for sample preparation for enzyme-substrate based bioassay such as NBS assays for lysosomal storage diseases (LSDs). Lysosomal enzymes are modified during synthesis by high mannose oligosaccharides at specific asparagine residues (N-glycosylation). Because the lysosomal enzymes are N-glycosylated, immobilization with ConA may be used to enrich and concentrate the enzymes in a complex biological sample, such as a dried blood spot (DBS) sample.

In another example, the methods of the invention may be used to reduce, preferably entirely eliminate, contaminates that may inhibit enzyme activity and cause false positive readings in screening assays (e.g., NBS assays) and diagnostic tests. In various embodiments, magnetically responsive ConA beads are used to reduce, preferably entirely eliminate, contaminants and concentrate N-glycosylated molecules of a biological sample prior to performing a screening assay or diagnostic test.

7.1 Enzyme Concentration

Concanavalin A (ConA) is a lectin that specifically binds glucose and/or mannose residues containing unmodified hydroxyl residues at positions C3, C4, and C6 (i.e., N-glycans of high mannose type, hybrid type, and bi-antennary complex type). In one example, ConA that is immobilized on magnetically responsive beads may be used for enrichment of N-glycosylated proteins (i.e., proteins containing mannose residues in their oligosaccharide side chains) from complex biological samples. N-glycoproteins are non-covalently bound to ConA without loss of activity and/or stability. Non-glycosylated and O-glycosylated molecules are not bound by ConA and are removed from the sample in subsequent steps. Because ConA bound N-glycoproteins are active/stable, bead-bound enzymatic activity (e.g., lysosomal enzyme activity) may be analyzed directly. Alternatively, bound glycoprotein (e.g., lysosomal enzymes) may be released from the ConA beads prior to analysis. Enrichment of N-glycosylated proteins (e.g., lysosomal enzymes) by ConA immobilization may be used to substantially improve the detection of less abundant N-glycosylated proteins in a complex biological sample, such as a DBS sample.

In one embodiment, ConA magnetically responsive beads, such as SiMAG-ConA beads (available from chemicell GmbH) and elution buffer chemistries may be used to enrich and purify N-glycosylated proteins. In one example, N-glycosylated proteins (e.g., lysosomal enzymes) bound to SiMAG-ConA magnetically responsive beads may be released (eluted) from the beads by competition with sugars (e.g., methyl-α-D-mannopyranoside). In another example, glycomimetics may be used to elute N-glycosylated proteins (e.g., lysosomal enzymes) from magnetically responsive ConA beads. FIG. 1 shows a structure 100 of an example of a glycomimetic (NSC 120634) that is an effective inhibitor (competitor) of ConA-carbohydrate binding. NSC 120634, a compound in the National Cancer Institute Diversity Set, is at least 20 times more effective at inhibiting ConA-carbohydrate binding than methyl-α-D-mannopyranoside. Glycomimetics, such as NSC 120634, may be used to effectively elute newborn screening enzyme targets (e.g., lysosomal enzymes) bound to magnetically responsive ConA beads.

Figure 2:
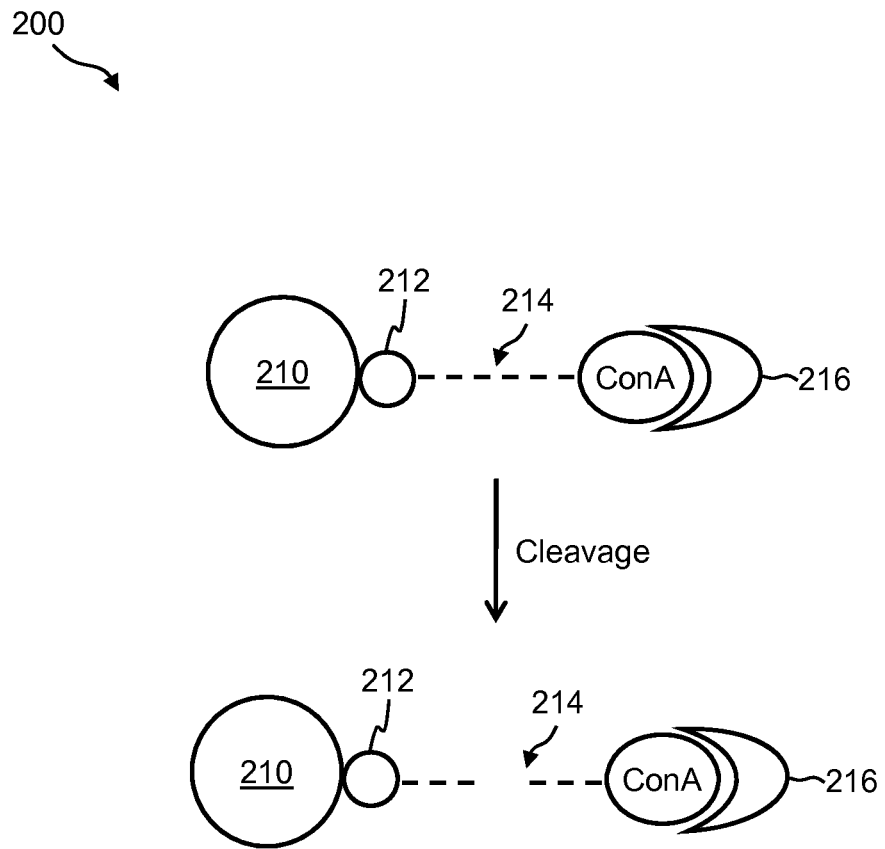
FIG. 2 illustrates an example of a process of releasing ConA-bound molecules from magnetically responsive beads.

In another embodiment, a cleavable bond positioned between magnetically responsive beads and ConA may be used to release (elute) ConA-bound molecules from the magnetically responsive beads. FIG. 2 illustrates a process 200, which is an example of a process of releasing ConA-bound molecules from magnetically responsive beads. A magnetically responsive bead 210 may be coated with an anchor molecule 212 that forms a readily cleavable bond 214 with ConA or a modified version of ConA. An N-glycosylated protein 216 may be anchored on magnetically responsive beads 210 through binding with ConA. N-glycosylated protein 216 may, for example, be a lysosomal enzyme. A ConA-bound N-glycosylated protein 216 complex may be released from magnetically responsive bead 210 by cleavage (disruption) of cleavable bond 214.

In one embodiment, a readily cleavable bond may be formed using a biotin-streptavidin coupling. In one example, anchor molecule 212 may be a streptavidin molecule that forms cleavable bond 214 with biotinylated ConA. Upon disruption of cleavable bond 214, a biotinylated ConA-glycosylated protein 216 complex is released. In another example, anchor molecule 212 may be a biotin molecule that forms cleavable bond 214 with a streptavidin-modified ConA. Upon disruption of cleavable bond 214, a streptavidin-ConA-glycosylated protein 216 complex is released. The ConA-protein complexes (e.g., [biotin]-[ConA]-[protein] or [streptavidin]-[ConA]-[protein]) may be separated from the magnetically responsive beads and analyzed using on-bench or on-actuator NBS assay protocols.

7.1.1 On-Bench Concentration Protocol

In one embodiment, samples for newborn testing for metabolic disorders may be prepared on-bench using magnetically responsive ConA beads to concentrate N-glycosylated proteins. The concentrated sample may be subsequently released from the ConA beads and analyzed using on-bench NBS assay protocols or loaded onto a fluid reservoir of a droplet actuator and analyzed using digital microfluidic NBS assay protocols.

An example of an on-bench concentration protocol for N-glycosylated proteins (e.g., enzymes) using magnetically responsive ConA beads (e.g., SiMAG-ConA beads), and DBS extracts may include, but is not limited to, the following steps: Place a 3 mm DBS sample punch in 100 µL of extraction buffer (e.g., PBS pH 6.0, 0.1% w/v Tween® 20) in a well of a 96-well, round bottom plate and incubate for 30 minutes at room temperature on an orbital shaker. Multiple DBS sample punches may be extracted to provide sufficient sample volume for multiple ConA bead binding reactions. For example, for 12 ConA bead binding reactions, 14 DBS punches may be extracted to provide additional extract for adjusting bead binding volume to 100 µL. At the end of the extraction, aliquot 100 µL of DBS extract to a tube containing a quantity (e.g., about 1 µL to about 10 µL to about 20 µL) of magnetically responsive ConA beads and incubate for about 30 minutes at room temperature with end-over-end rotation. Collect the magnetically responsive ConA beads to the bottom of the tube using a magnet. Pipette the supernatant (e.g., about 100 µL) containing unbound material from the tube and discard to waste. Bead-bound enzymatic activity may be analyzed directly or bound glycoproteins (enzymes) may be released from the ConA beads prior to analysis. To evaluate bead-bound enzymatic activity, add 10 µL of 1 mM acetate buffer pH 5.0 containing 0.1% Tween 20 to the tube to the beads and transfer the resuspended beads to a separate well of a 96-well microtiter plate. Alternatively, the resuspended beads (about 10 µL) may be loaded onto a fluid reservoir of a droplet actuator and analyzed using digital microfluidic NBS assay protocols. To release bound molecules from ConA beads (e.g., SiMAG-ConA beads) prior to analysis, the collected beads may be resuspended, for example, in about 10 µL of elution buffer that contains a sufficient concentration of a competing molecule, such as the sugar methyl-α-D-mannopyranoside, and incubated with occasional flicking for 10 minutes. At the end of the incubation period, the magnetically responsive ConA beads may be collected at the bottom of the tube using a magnet. The eluate (about 10 µL) may be removed from the tube and placed in a separate well of a 96-well plate for subsequent on-bench analysis. Alternatively, the eluate (about 10 µL) may be loaded onto a fluid reservoir of a droplet actuator and analyzed using digital microfluidic NBS assay protocols.

7.1.2 On-Actuator Concentration Protocols

In another embodiment, samples for newborn testing for metabolic disorders may be concentrated and collected using ConA magnetically responsive beads on a droplet actuator. A bead concentration protocol may be used to concentrate and collect N-glycosylated proteins in the sample volume in a fluid reservoir in fluid communication with an opening for flowing liquid from the reservoir into the droplet operations gap of the droplet actuator. Sample input dispensing electrodes and reservoirs of the droplet actuator may be designed for a larger sample input volume (e.g., about 80 to about 200 µL). One or more magnets may be arranged in proximity of sample input dispensing electrodes and reservoirs for concentration and collection of a quantity of magnetically responsive beads (e.g., magnetically responsive ConA beads). The magnet(s) may be a stationary magnet or a movable magnet.

In one example, a bead concentration protocol may be used to concentrate and collect N-glycosylated proteins in the sample volume in an off-actuator sample reservoir. A quantity (e.g., about 2 to 3 µL) of magnetically responsive ConA beads may be added to the large sample volume (e.g., about 100 µL to about 200 µL), prior to loading the sample onto an off-actuator sample reservoir in fluid communication with an opening for flowing liquid from the reservoir into the droplet operations gap of the droplet actuator. The large volume sample may then be processed on-actuator using a bead concentration protocol into a 1× to 4× droplet (i.e., about 100 nL to about 1320 nL droplet depending on the size of the droplet operations electrodes). In another example, a large sample volume may be concentrated in an on-actuator sample reservoir. In this example, a series of sample droplets (e.g., 660 nL sample droplets) may be sequentially incubated in an on-actuator sample reservoir using a single reagent droplet that contains a quantity of magnetically responsive ConA beads. Specialized mixing electrodes may be used to facilitate bead mixing. Because of the flexibility and programmability of a digital microfluidics, a sample processing protocol may be readily adapted for on-actuator, off-actuator, or any combination of sample processing. Once the concentrated magnetically responsive bead droplet is formed, it may be subjected to other droplet operations within the droplet actuator (e.g., bead washing and elution of bead-bound molecules; digital microfluidic NBS assay protocols).

An example of an off-actuator concentration protocol for N-glycosylated proteins using magnetically responsive ConA beads and DBS extracts includes, but is not limited to, the following steps: Place one 3 mm DBS sample punch in 100 µL of extraction buffer (e.g., PBS pH 6.0, 0.1% w/v Tween® 20) in a well of a 96-well round bottom plate and incubate for 30 minutes at room temperature on an orbital shaker. At the end of the extraction, aliquot 100 µL of DBS extract to a tube containing a quantity (e.g., about 1 to about 20 µL) of magnetically responsive ConA beads and transfer the bead-containing sample to a sample reservoir in fluid communication with an opening for flowing liquid from the reservoir into the droplet operations gap of the droplet actuator. The large volume sample may then be incubated and processed on-actuator using a bead concentration protocol into a smaller sample droplet into a 1× to 4× droplet (i.e., about 100 nL to about 1320 nL droplet depending on the size of the droplet operations electrodes). Bead-bound enzymatic activity may be analyzed directly or bound glycoproteins (enzymes) may be released from the ConA beads using, for example, a bead washing and elution protocol, prior to analysis. Concentrated samples may be dispensed into one or more subsamples and analyzed using one or more digital microfluidic NBS assay protocols.

7.1.3 Bead Binding and Elution Parameters for DBS Samples

Parameters that may be varied in a concentration protocol for DBS samples that use magnetically responsive ConA, such as SiMAG-ConA beads, may include, but are not limited to, composition and volume of DBS extraction buffer, number of DBS punches (e.g., 1, 2, or 3 punches), quantity of magnetically responsive ConA beads (e.g., 1, 5, 10, or 20 µL), bead incubation time (e.g., 15, 30, or 60 minutes), composition of binding buffer (e.g., mannose; NaCl; EDTA to chelate metal ions and subsequent addition of metal ions such as ZnCl) and composition of elution buffer (e.g., 10, 20, 50 mM or higher concentrations of methyl-α-D-mannopyranoside; 1 mM acetate pH 5.5).

To evaluate the effect of extraction buffer composition and ConA-bead volume in NBS assays, DBS extracts were prepared from quality control (QC) dried blood spot samples (i.e., base pool (QC-BP), low (QC-Low), medium (QC-Med), and high (QC-H) activity samples). The QC samples were prepared as described in reference to FIG. 19. The base pool (BP) QC sample was prepared from a pool of leukoreduced human red blood cells that was adjusted with serum to a hematocrit of 50%. The High (H) activity QC sample was prepared from pooled cord blood that was adjusted with serum to a hematocrit of 50%. The BP sample is used as a control for hydrolysis non-specific to white blood cell lysosomal enzymes (background control). Each DBS sample was placed in a separate well of a 96-well plate. Extracts of DBS samples were prepared using either phosphate buffered saline (PBS) pH6.0 containing 0.1% Tween® 20; water containing 0.1% Tween® 20; or 1 mM Acetate, 50 mM NaCl pH 5.5 containing 0.1% Tween® 20 as extraction buffers. The DBS extracts were analyzed using on-bench assay protocols for Niemann Pick, Gaucher, Krabbe, Pompe, Fabry, Hunter, and Hurler disorders.

The on-bench assay protocol for evaluating the efficacy of extraction buffer composition and ConA-bead volume in NBS assays using DBS samples included, but is not limited to, the following steps: 3 mm DBS sample punches were placed in 100 µL of extraction buffer (e.g., PBS pH 6.0, 0.1% w/v Tween® 20; water, 0.1% Tween® 20; or 1 mM Acetate, 50 mM NaCl pH 5.5, 0.1% Tween® 20) in separate wells of a 96-well round bottom plate and incubated for 30 minutes at room temperature on an orbital shaker. At the end of the extraction, 100 µL of DBS extract was transferred from each well to separate tubes containing a quantity (e.g., 20, 10, 5, or 1 µL) of magnetically responsive SiMAG-ConA beads and incubated for 25 to 30 minutes at room temperature with end-over-end rotation. A 10 µL aliquot of each extract supernatant was transferred from the tube to separate wells of a 96-well plate. The remaining supernatant from each tube was transferred to waste. The beads were resuspended in 10 µL of 1 mM acetate buffer pH 5.0 containing 0.1% Tween 20 and transferred to separate wells of the 96-well plate. Aliquots of bead controls (i.e., 20, 10, 5, or 1 µL ConA beads only, washed and resuspended in 10 µL of 1 mM acetate buffer pH 5.0 containing 0.1% Tween 20) were placed in designated wells of the 96-well plate. Enzyme substrate (10 µL) was added to each sample and control well and mixed for 20 seconds on an orbital shaker. The reactions were incubated at 37° C. for 20 hrs (overnight). At the end of the incubation period, 50 µL stop buffer was added to all sample and control wells, and fluorescence read.

Figure 3:
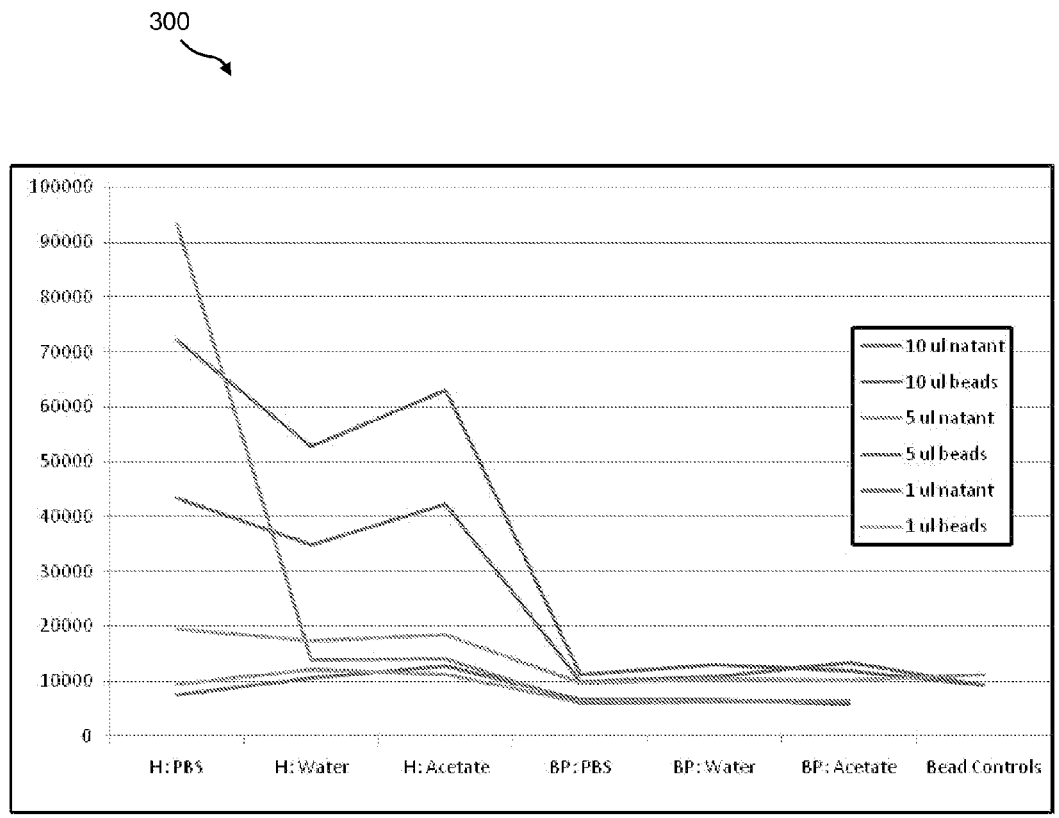
FIG. 3 shows an example of a plot of the effect of extraction buffer composition and ConA bead volume in a Niemann Pick assay for acid sphingomyelinase activity using DBS.

FIG. 3 shows a plot 300, which is an example of a plot of the effect of extraction buffer composition and ConA bead volume in a Niemann Pick assay for acid sphingomyelinase activity using DBS. The data associated with plot 300 is shown in Table 1. The stop buffer in the Niemann Pick assay was 0.2 M Sodium bicarbonate pH 10.1 with 0.25% w/v Triton X-100. The HMU substrate in the Niemann Pick assay was 6-hexadecanoyl-4-methylumbelliferyl-phosphorylcholine (HMU-PC; available from Moscerdam Substrates). A 5.6 mM HMU-PC stock solution was prepared in NP buffer (0.1 M Acetate buffer, pH 5.2 with 0.5% (w/v) sodium taurocholate sodium salt hydrate, and 0.25 mM zinc chloride). The HMU-PC stock solution was heated briefly (until clear) in a 60° C. water bath, aliquoted and stored at −80° C. A working solution of Niemann Pick substrate was prepared by heating a frozen aliquot of HMU-PC stock solution at 60° C. until clear and diluting 20 µL of the stock substrate with 100 µL NP buffer to a final volume of 120 µL. The working solution of Niemann Pick substrate was used immediately. HMU fluorescence was read at 400/460 excitation/emission at a gain of 75. The data show extraction of DBS punches in acetate extraction buffer (1 mM Acetate, 50 mM NaCl pH 5.5, 0.1% Tween® 20) provided higher levels of enzyme activity in QC-H supernatant samples compared to QC-BP samples (background controls). However, extraction of DBS punches in PBS extraction buffer (PBS pH6.0 containing 0.1% Tween® 20) provided higher levels of bead-bound enzyme activity in all QC-H samples (i.e., 10, 5, or 1 µL ConA beads) compared to QC-BP samples (background control). The highest level of bead-bound enzyme activity was observed with 10 µL ConA beads in QC-H DBS samples extracted in PBS buffer.

TABLE 1

Effect of DBS extraction buffer composition on Niemann Pick assay

| µL Beads | QC-H | | | QC-BP | | | Bead Control |
|---|---|---|---|---|---|---|---|
| | PBS | Water | Acetate | PBS | Water | Acetate | |
| 10 µL supernatant* | 7441 | 10600 | 12665 | 6532 | 6673 | 5777 | |
| 10 µL beads† | 72208 | 52870 | 63019 | 11126 | 12916 | 11839 | 9336 |
| 5 µL supernatant | 9427 | 12076 | 11241 | 6133 | 6495 | 6444 | |
| 5 µL beads | 43454 | 34897 | 42280 | 9931 | 10875 | 13433 | 9340 |
| 1 µL supernatant | 93352§ | 13890 | 14112 | 5876 | 6262 | 6115 | |
| 1 µL beads | 19422 | 17297 | 18483 | 9587 | 10433 | 10171 | 11119 |

*supernatant: enzyme activity not bound to ConA beads;
†beads: enzyme activity bound to ConA beads;
§ Data point was not in line with other experimental data and was disregarded in determining experimental conclusions.

Figure 4:
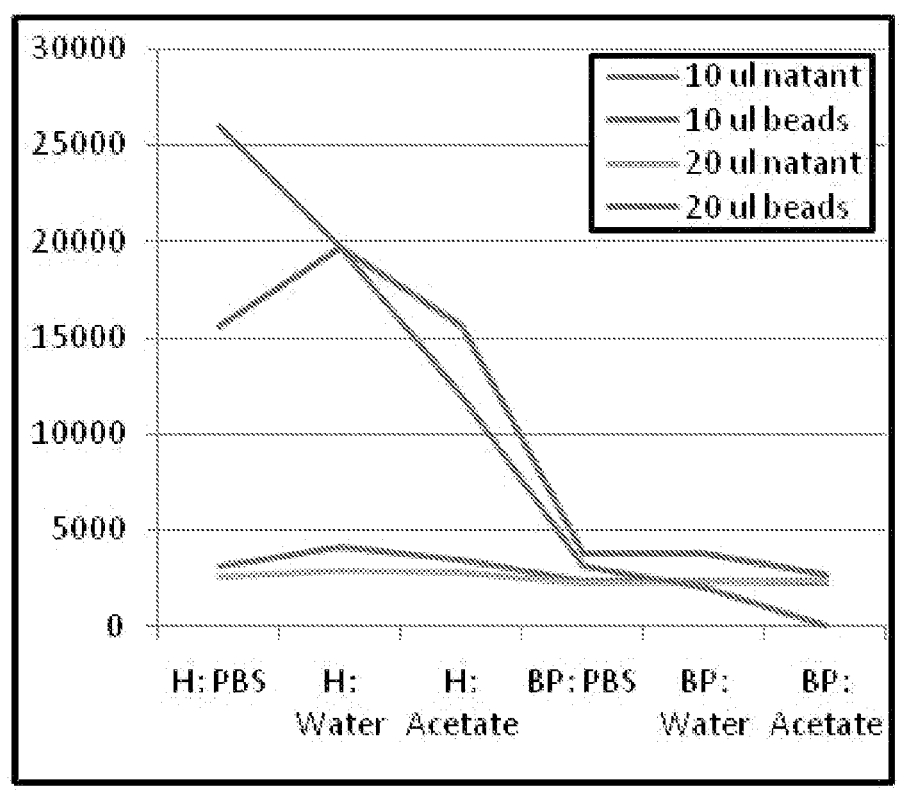
FIG. 4 shows an example of a plot of the effect of extraction buffer composition and ConA bead volume in a Krabbe assay for galactocerebrosidase activity using DBS.

FIG. 4 shows a plot 400, which is an example of a plot of the effect of extraction buffer composition and ConA bead volume in a Krabbe assay for galactocerebrosidase activity using DBS. The data associated with plot 400 is shown in Table 2. The stop buffer in the Krabbe assay was 0.2 M Sodium bicarbonate pH 10.1 with 0.25% w/v Triton X-100. The HMU substrate in the Krabbe assay was 6-hexadecanoylamino-4-methylumbelliferyl-β-D-galactoside (HMU-βGal; available from Moscerdam Substrates). A HMU-βGal stock film was prepared by combining in a glass vial 42 µL of a 12.7 mM stock solution of HMU-βGal in 2:1 chloroform:methanol (v/v) with 8.04 µL pure oleic acid, 200 µL 10% (w/v) sodium taurocholate in 2:1 chloroform:methanol, and 75 µL 2:1 chloroform:methanol and vortexed vigourously. Aliquots (100 µL) were transferred to small glass vials and dried overnight under a chemical hood. The dried films were stored at −80° C. for up to 6 months. A working solution of Krabbe substrate was prepared by reconstituting one film (one vial) in 100 µL 0.1 M/0.2 M Citrate/Phosphate buffer, pH 5.2 and vortexing vigorously for 30 to 60 seconds until micelles were formed as indicated by a fine, cloudy appearance. The working solution of Krabbe substrate was used immediately. HMU fluorescence was read at 400/460 excitation/emission at a gain of 75. The data show 20 µL of ConA beads added to QC-H DBS samples extracted in PBS, water, or Acetate extraction buffers substantially removes galactocerebrosidase activity from the supernatant relative to enzyme activity in QC-BP supernatant samples. A 10 μL aliquot of ConA beads may also be sufficient to significantly remove enzyme from sample supernatants.

TABLE 2

Effect of DBS extraction buffer composition on Krabbe assay

| μL Beads | QC-H | | | QC-BP | | | Bead Control |
|---|---|---|---|---|---|---|---|
| | PBS | Water | Acetate | PBS | Water | Acetate | |
| 10 μL supernatant* | 3180 | 4168 | 3439 | 2391 | 2409 | 2233 | |
| 10 μL beads† | 15602 | 19735 | 15611 | 3776 | 3760 | 2670 | 4662 |
| 20 μL supernatant | 2620 | 2860 | 2795 | 2261 | 2391 | 2366 | |
| 20 μL beads | 25982 | 19739 | 11966 | 3151 | 2030 | 0 (no substrate) | 3772 |

Figure 5A:
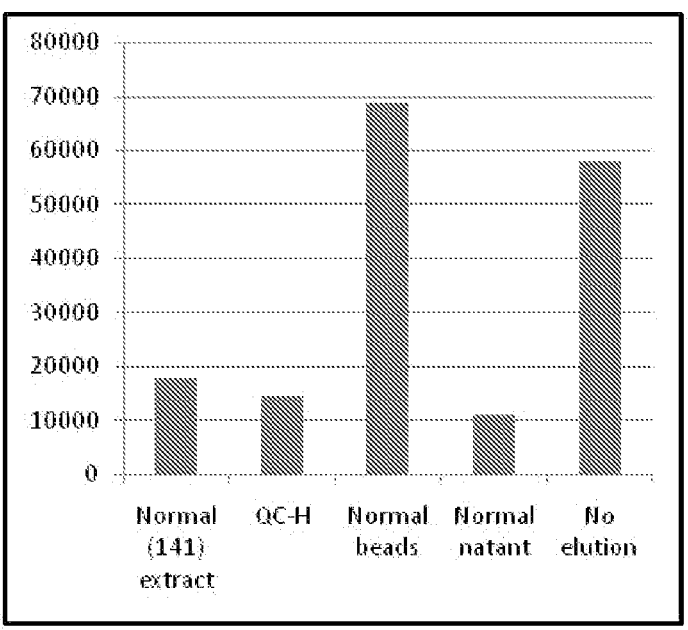
FIGS. 5A and 5B show examples of a graph and a plot, respectively, of the effect of elution buffer composition in a Niemann Pick assay using DBS.
Figure 5B:
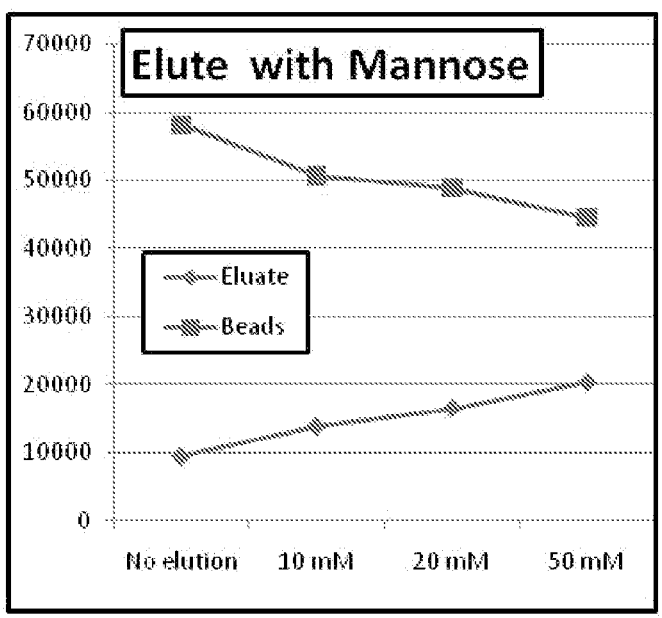

*supernatant: enzyme activity not bound to ConA beads;
†beads: enzyme activity bound to ConA beads To evaluate the effect of elution buffer composition in NBS assays, QC-H and normal (not heat denatured) DBS extracts were prepared using PBS pH6.0 containing 0.1% Tween® 20 as the extraction buffer. FIGS. 5A and 5B show a graph 500 and a plot 550, respectively, which are examples of a graph and a plot of the effect of elution buffer composition in a Niemann Pick assay using DBS. The data associated with graph 500 and a plot 550 is shown in Table 3. The on-bench assay included the following steps: 3 mm DBS sample punches were placed in 100 μL of PBS pH 6.0, 0.1% w/v Tween® 20 in separate wells of a 96-well round bottom plate and incubated for 30 minutes at room temperature on an orbital shaker. At the end of the extraction, 100 μL of DBS extract was transferred from each well to separate tubes containing a 10 μL of magnetically responsive SiMAG-ConA beads and incubated for 30 minutes at room temperature with end-over-end rotation. The tubes were placed on a magnet and the magnetically responsive ConA beads were collected at the bottom of the tube. The supernatant (about 100 μL) was removed from the tube and discarded to waste. The beads were resuspended in 10 μL of elution buffer containing 10, 20, or 50 mM methyl-α-D-mannopyranoside in PBS pH 6.0 containing 0.1% w/v Tween 20 and incubated with occasional flicking for 10 minutes. At the end of the incubation period, the tubes were placed on a magnet and the magnetically responsive ConA beads were collected at the bottom of the tube. The eluate (10 μL) was removed from each tube and placed in separate wells of a 96-well plate. Niemann Pick enzyme substrate (10 μL; 20 μL substrate stock in 100 μL Niemann Pick (NP) buffer) was added to each sample well and mixed for 20 seconds on an orbital shaker. The reactions were incubated at 37° C. for 20 hrs (overnight). At the end of the incubation period, 50 μL of stop buffer (0.2 M sodium bicarbonate, pH 10.1 containing 0.25% Triton X) was added to all samples and the fluorescence of HMU read at 400/460 excitation/emission at a gain of 75. The data show that increasing concentrations of methyl-α-D-mannopyranoside release acid sphingomyelinase activity from ConA beads into the sample eluate. The data also suggests that the presence of up to 50 mM methyl-α-D-mannopyranoside does not inhibit the enzymatic assay. Higher concentrations of methyl-α-D-mannopyranoside may be selected to substantially increase the release (i.e., greater than 25% of QC-H values) of bound enzyme activity from ConA beads.

TABLE 3

Effect of elution buffer composition on Niemann Pick assay

| | | | Eluate | Beads |
|---|---|---|---|---|
| Normal (141) extract | 17956, 18785 | | | |
| QC-H | 14568, 13502 | No elution | 9462 | 58163 |
| | | 10 mM | 13876 | 50635 |
| Normal beads | 68898 | 20 mM | 16486 | 48916 |
| Normal natant | 11113 | 50 mM | 20340 | 44573 |

Figure 6:
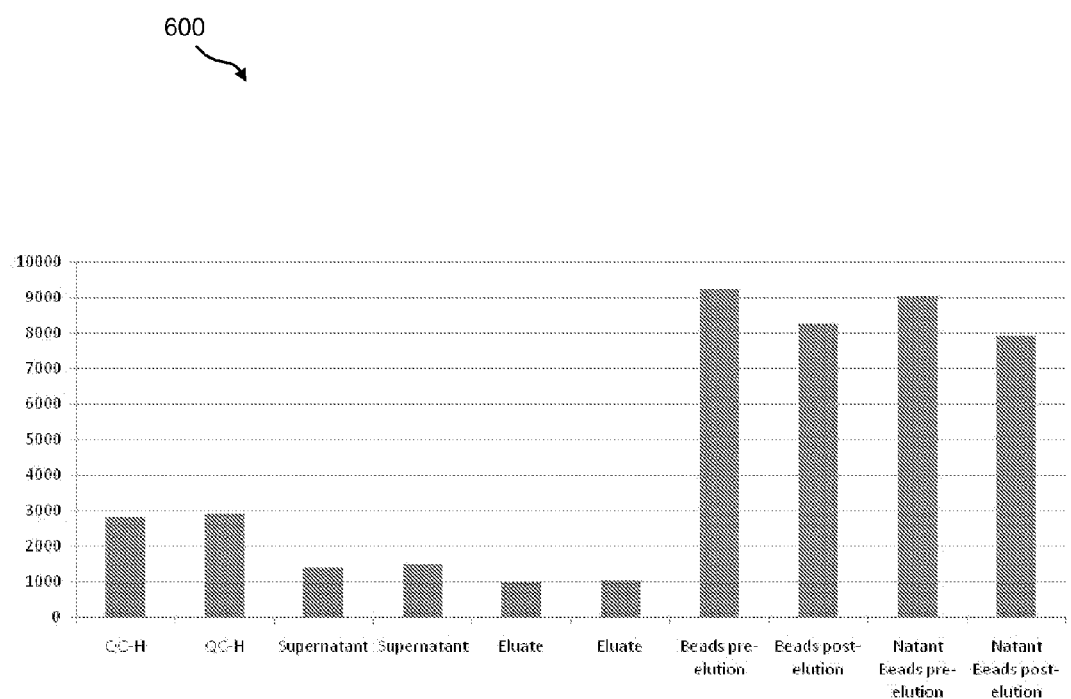
FIG. 6 shows an example of a bar graph of the effect of elution buffer composition in a Gaucher assay for acid β-D-glucosidase activity using DBS.

FIG. 6 shows a bar graph 600, which is an example of a bar graph of the effect of elution buffer composition in a Gaucher assay for acid β-D-glucosidase activity using DBS. The stop buffer in the Gaucher assay was 0.2 M Sodium bicarbonate pH 10.0 with 0.01% (w/v) Tween 20. The 4-MU substrate in the Gaucher assay was 4-Methylumbelliferyl-β-D-Glucopyranoside (4-MU-β-Gluc). A 700 mM 4-MU-β-Gluc stock solution was prepared in DMSO and stored in single-use aliquots at −80° C. To prepare a working solution of Gaucher enzyme substrate, 4 μL of 4-MU-β-Gluc stock solution was added to 0.1 M/0.2 M citrate/phosphate buffer, pH 5.2 containing 1.5% (w/v) sodium taurocholate and 0.01% (w/v) Tween 20. The working substrate solution was mixed well and used immediately. For the Gaucher assay, 3 QC-H DBS sample punches were placed in 100 μL of PBS pH 6.0, 0.1% (w/v) Tween® 20 in separate wells of a 96-well round bottom plate and incubated for 30 minutes at room temperature on an orbital shaker. At the end of the extraction, the QC-H extracts were pooled into a single tube. For the SiMAG-ConA bead binding procedure, 100 μL aliquots of pooled QC-H DBS extract were transferred to two separate tubes each containing 10 μL ConA beads and incubated for 30 minutes at room temperature with end-over-end rotation. A third tube containing 100 μL of pooled QC-H DBS extract was used as an unbound control. The tubes containing ConA beads were placed on a magnet and the magnetically responsive ConA beads were collected at the bottom of the tube. An aliquot of the each supernatant (about 10 μL) was transferred to designated wells of a 96-well plate. The rest of the supernatant was discarded to waste. The beads in one tube were resuspended in 10 μL of 1 mM acetate buffer pH 5.5 containing 0.1% (w/v) Tween 20 and placed in a designated well of the 96-well plate. The beads in the second tube were resuspended in 10 μL of elution buffer (PBS pH 6.0, 0.1% (w/v) Tween 20) containing 10 mM methyl-α-D-mannopyranoside and incubated on a rotator platform for 10 minutes. At the end of the incubation period, the tube was placed on a magnet and the magnetically responsive ConA beads were collected at the bottom of the tube. The eluate (about 10 μL) was removed from the tube and placed in a separate well of the 96-well plate. The eluted beads were resuspended in 10 μL of 1 mM acetate buffer pH 5.5 containing 0.1% (w/v) Tween 20 and placed in a designated well of the 96-well plate. Duplicate aliquots (about 10 μL) of the unbound pooled QC-H DBS extract were transferred to designated wells of the 96-well plate. Enzyme substrate (10 μL) was added to each sample and control well and mixed for 20 seconds on an orbital shaker. The reactions were incubated at 37° C. for 20 hrs (overnight). At the end of the incubation period, 50 μL stop buffer was added to all sample and control wells, and 4-MU fluorescence read at 360/460 excitation/emission at a gain of 50. The data show acid β-D-glucosidase enzyme activity in DBS extracts is bound by SiMAG-ConA beads concentrating the enzyme activity about 6-7× increase relative to unbound pooled DBS extract. Greater than 10 mM methyl-α-D-mannopyranoside may be required for sufficient elution of Gaucher enzyme (acid β-D-glucosidase) bound to magnetically responsive ConA beads.

To evaluate the effect of extraction buffer and ConA bead binding on α-glucosidase (Pompe) and β-galactosidase (Fabry) enzyme activities, QC-BP, QC-Low, QC-Med, and QC-H DBS samples were extracted in either PBS pH 6.0, 0.1% w/v Tween® 20 or water, 0.1% Tween® 20. The on-bench assay protocol included the following steps: For each DBS QC sample (i.e., QC-BP, QC-Low, QC-Med, and QC-H), three punches were extracted in either 100 µL each water, 0.1% Tween® 20 or in 100 µL each of PBS pH 6.0, 0.1% (w/v) Tween® 20 in separate wells of a 96-well round bottom plate. The DBS punches were incubated for 30 minutes at room temperature on an orbital shaker. At the end of the extraction, extracts for each QC-BP, QC-Low, QC-Med, and QC-H samples were pooled. Duplicate 10 µL aliquots of each pooled DBS sample were transferred to separate wells of a 96-well microtiter plate (i.e., duplicate aliquots of unbound extract prepared in extraction buffer and unbound extract prepared in PBS pH 6.0, 0.1% (w/v) Tween® 20). A second set of duplicate 100 µL aliquots of each pooled DBS sample were transferred to separate tubes containing a 10 µL of magnetically responsive SiMAG-ConA beads and incubated for 30 minutes at room temperature with end-over-end rotation. The tubes were placed on a magnet and the magnetically responsive ConA beads were collected at the bottom of the tube. The supernatant (about 100 µL) was removed from the tube and discarded to waste. The beads were resuspended in 10 µL of assay buffer and transferred to separate wells of the 96-well microtiter plate. Enzyme substrate (10 µL) was added to each sample well and mixed for 20 seconds on an orbital shaker. For the α-glucosidase (Pompe) assay the 4-MU substrate was 4-methylumbelliferyl α-D-glucopyranoside. To prepare a working solution of Pompe enzyme substrate, 30 µL of Pompe inhibitor (3 µL of inhibitor stock in 197 µL of Pompe buffer) and 21.4 µL of Pompe enzyme substrate was added to 247.4 µL of Pompe buffer. For the β-galactosidase (Fabry) enzyme assay the 4-MU substrate was 4-methylumbelliferyl α-D-galactopyranoside. To prepare a working solution of Fabry enzyme substrate, 60 µL of Fabry inhibitor and 3.2 µL of Fabry enzyme substrate was added to 235.8 µL of Fabry buffer. The reactions were incubated at 37° C. for 20 hrs (overnight). At the end of the incubation period, 50 µL stop buffer (0.2 M Sodium bicarbonate pH 10.0 with 0.01% (w/v) Tween 20) was added to all sample wells, and fluorescence read at 360/460 excitation/emission at a gain of 50.

Figure 7A:
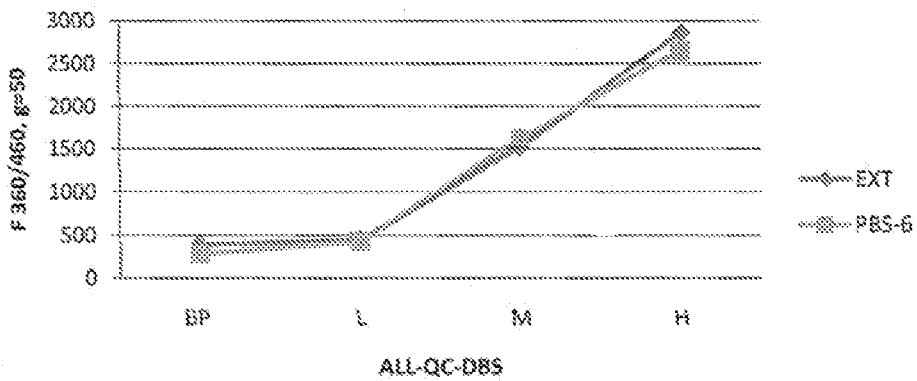
FIGS. 7A and 7B show examples of plots of α-glucosidase (Pompe) and β-galactosidase (Fabry) enzyme activities, respectively, in DBS extracts prepared on-bench using either water, 0.1% Tween® 20 (EXT) or PBS pH 6.0, 0.1% (w/v) Tween® 20.
Figure 7B:
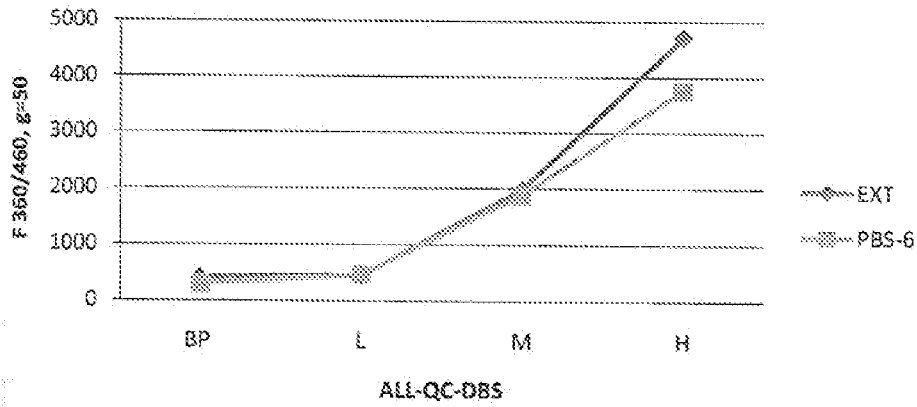

FIGS. 7A and 7B show plots 700 and 750, which are examples of plots of α-glucosidase (Pompe) and β-galactosidase (Fabry) enzyme activities, respectively, in DBS extracts prepared on-bench using either water, 0.1% Tween® 20 (EXT) or PBS pH 6.0, 0.1% (w/v) Tween® 20. The data associated with FIG. 7A is shown in Table 4. The data associated with FIG. 7B is shown in Table 5.

TABLE 4

Effect of DBS extraction buffer composition on Pompe assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 393 | 438 | 1523 | 2834 | 293 | 443 | 1647 | 2644 |
| 400 | 455 | 1518 | 2863 | 290 | 430 | 1609 | 2658 |
| Ave*: 397 | Ave: 447 | Ave: 1521 | Ave: 2849 | Ave: 292 | Ave: 437 | Ave: 1628 | Ave: 2651 |

*Ave = average

TABLE 5

Effect of DBS extraction buffer composition on Fabry assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 408 | 458 | 1953 | 4417 | 302 | 471 | 1887 | 3805 |
| 421 | 457 | 2002 | 5011 | 305 | 476 | 1905 | 3733 |
| Ave*: 415 | Ave: 458 | Ave: 1978 | Ave: 4714 | Ave: 304 | Ave: 474 | Ave: 1896 | Ave: 3769 |

*Ave = average

Figure 8A:
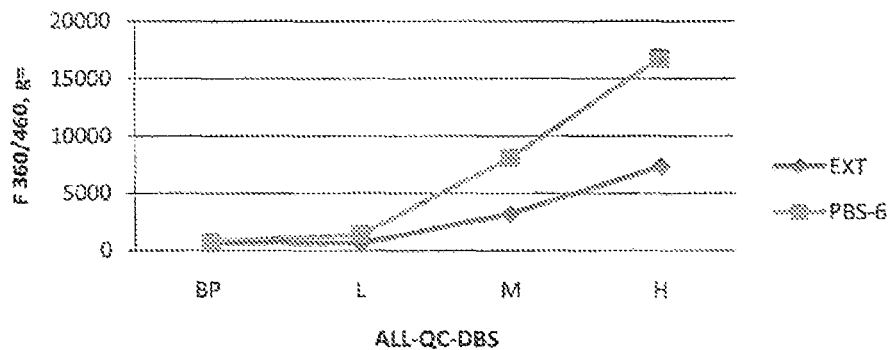
FIGS. 8A and 8B show examples of plots of α-glucosidase (Pompe) and β-galactosidase (Fabry) enzyme activities, respectively, in DBS extracts prepared on-bench using either water, 0.1% Tween® 20 (EXT) or PBS pH 6.0, 0.1% (w/v) Tween® 20 and an enzyme concentration step using ConA beads.
Figure 8B:
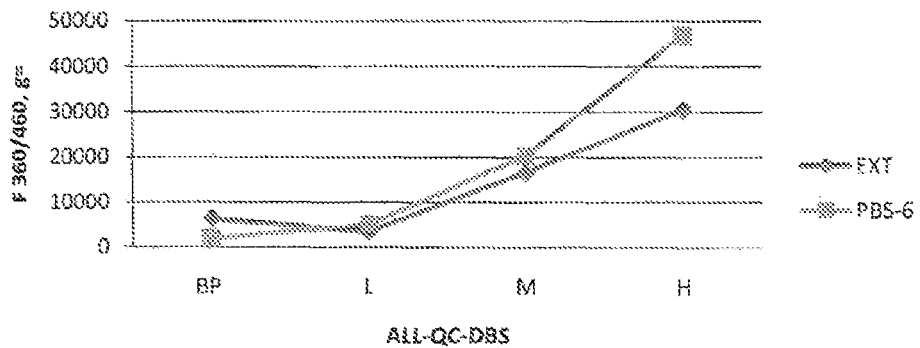

FIGS. 8A and 8B show plots 800 and 850, which are examples of plots of α-glucosidase (Pompe) and β-galactosidase (Fabry) enzyme activities, respectively, in DBS extracts prepared on-bench using either water, 0.1% Tween® 20 (EXT) or PBS pH 6.0, 0.1% (w/v) Tween® 20 and an enzyme concentration step using ConA beads. The data associated with FIG. 8A is shown in Table 6. The data associated with FIG. 8B is shown in Table 7. The data show increased binding of α-glucosidase (Pompe) and β-galactosidase (Fabry) enzymes to ConA beads in DBS samples extracted in PBS pH 6.0, 0.1% (w/v) Tween® 20.

TABLE 6

Effect of DBS extraction buffer composition on ConA bead binding in Pompe assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 648 | 609 | 3161 | 7314 | 835 | 1421 | 8136 | 16785 |

TABLE 7

Effect of DBS extraction buffer composition on ConA bead binding in Fabry assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 6336 | 3537 | 16678 | 30489 | 2077 | 5234 | 20499 | 47078 |

Figure 9A:
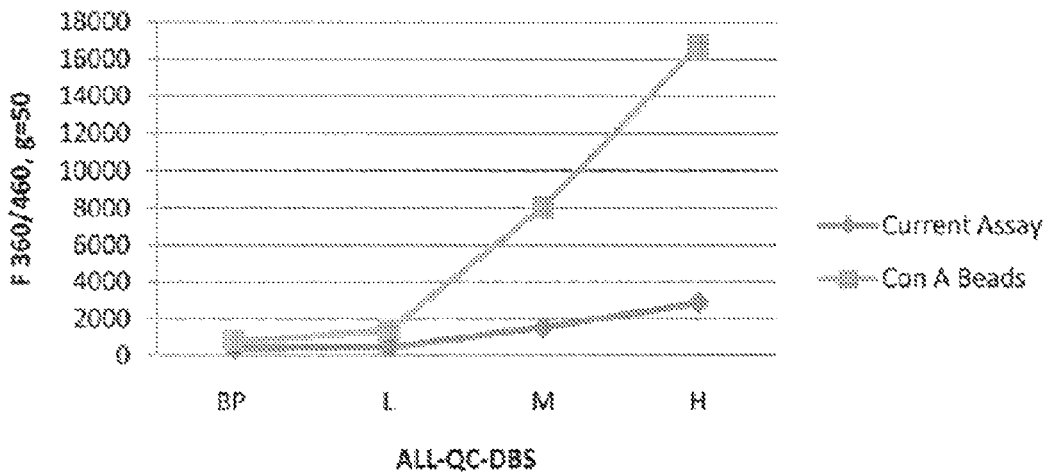
FIGS. 9A and 9B show examples of plots of α-glucosidase (Pompe) and β-galactosidase (Fabry) enzyme activities, respectively, in DBS extracts prepared on-bench with or without an enzyme concentration step using ConA beads.
Figure 9B:
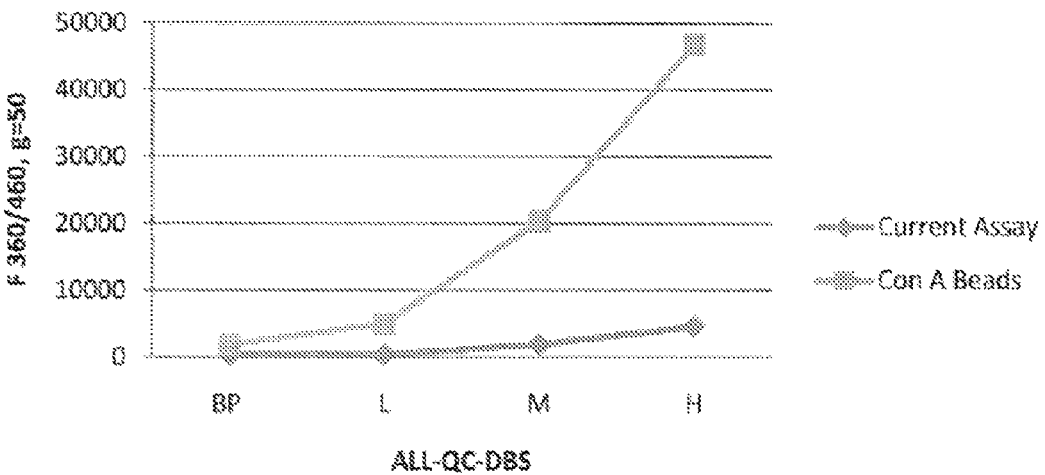

FIGS. 9A and 9B show plots 900 and 950, which are examples of plots of α-glucosidase (Pompe) and β-galactosidase (Fabry) enzyme activities, respectively, in DBS extracts prepared on-bench with or without an enzyme concentration step using ConA beads. In this example, DBS extracts were prepared using PBS pH 6.0, 0.1% (w/v) Tween® 20. The data show increased α-glucosidase (Pompe) and β-galactosidase (Fabry) enzyme activity in assays performed using a ConA bead binding concentration step.

To evaluate the effect of extraction buffer and ConA bead binding on idurondate-2-sulfatase (Hunter) and α-L-iduronidase (Hurler) enzyme activities, QC-BP, QC-Low, QC-Med, and QC-H DBS samples were extracted in either PBS pH 6.0, 0.1% w/v Tween® 20 or water, 0.1% Tween® 20. The on-bench assay protocol was essentially the same as described in reference to FIGS. 7 through 9 and Tables 4 through 7 except with the following changes: After ConA bead binding, beads in the Hunter reactions were resuspended in 10 μL 0.1 M Acetate pH 5 and transferred to designated wells of a 96-well plate. ConA beads in the Hurler reactions were resuspended in 0.04 M Acetate pH 3.5 and transferred to designated wells of a 96-well plate. For the idurondate-2-sulfatase (Hunter) assay the 4-MU substrate was 4-methylumbelliferyl α-L-iduronic acid-2-sulfate. For the α-L-iduronidase (Hurler) enzyme assay the 4-MU substrate was 4-methylumbelliferyl α-L-iduronic acid.

Figure 10A:
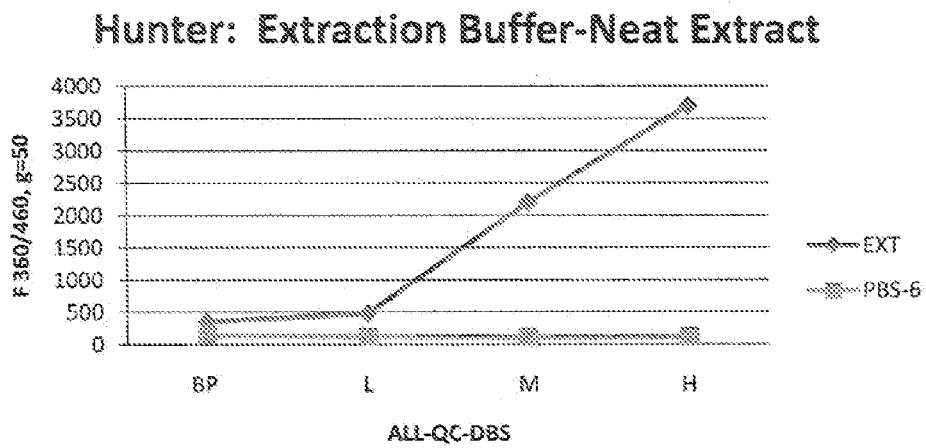
FIGS. 10A and 10B show examples of plots idurondate-2-sulfatase (Hunter) and α-L-iduronidase (Hurler) enzyme activities, respectively, in DBS extracts prepared on-bench using either water, 0.1% Tween® 20 (EXT) or PBS pH 6.0, 0.1% (w/v) Tween® 20.
Figure 10B:
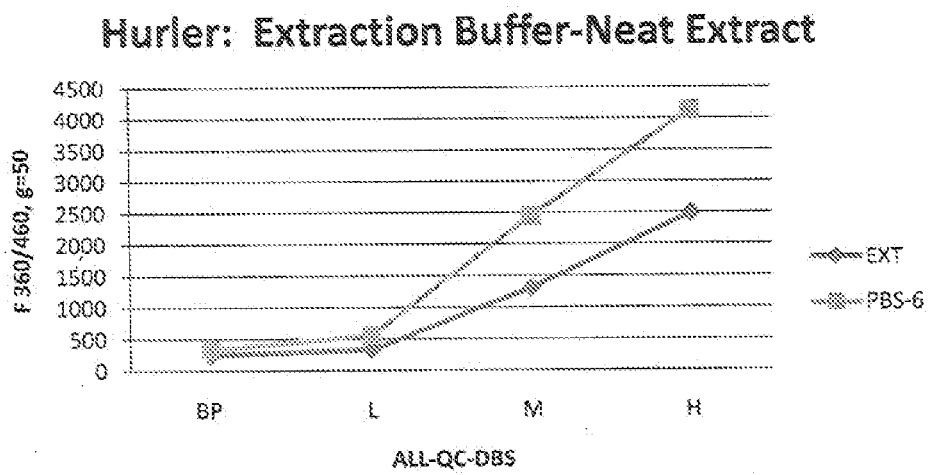

FIGS. 10A and 10B show plots 1000 and 1050, which are examples of plots idurondate-2-sulfatase (Hunter) and α-L-iduronidase (Hurler) enzyme activities, respectively, in DBS extracts prepared on-bench using either water, 0.1% Tween® 20 (EXT) or PBS pH 6.0, 0.1% (w/v) Tween® 20. Enzyme assays were performed in the extraction buffers. The data associated with FIG. 10A is shown in Table 8. The data associated with FIG. 10B is shown in Table 9. Referring to FIG. 10A and Table 8, the data show idurondate-2-sulfatase (Hunter) enzyme activity is inhibited in assays performed in PBS pH 6.0, 0.1% (w/v) Tween® 20 DBS extraction buffer. Referring to FIG. 10B and Table 9, the data show α-L-iduronidase (Hurler) enzyme activity is higher in assays performed in PBS pH 6.0, 0.1% (w/v) Tween® 20 DBS extraction buffer compared to assays performed in water, 0.1% Tween® 20 (EXT).

Figure 11A:
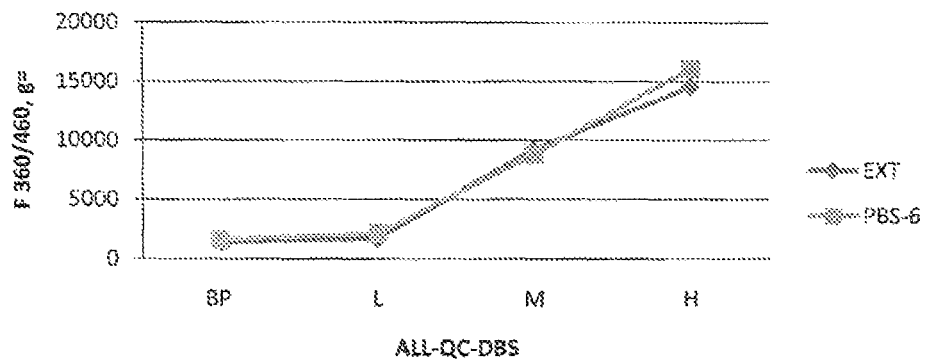
FIGS. 11A and 11B show examples of plots of idurondate-2-sulfatase (Hunter) and α-L-iduronidase (Hurler) enzyme activities, respectively, in DBS extracts prepared on-bench using either water, 0.1% Tween® 20 (EXT) or PBS pH 6.0, 0.1% (w/v) Tween® 20 and an enzyme concentration step using ConA beads.
Figure 11B:
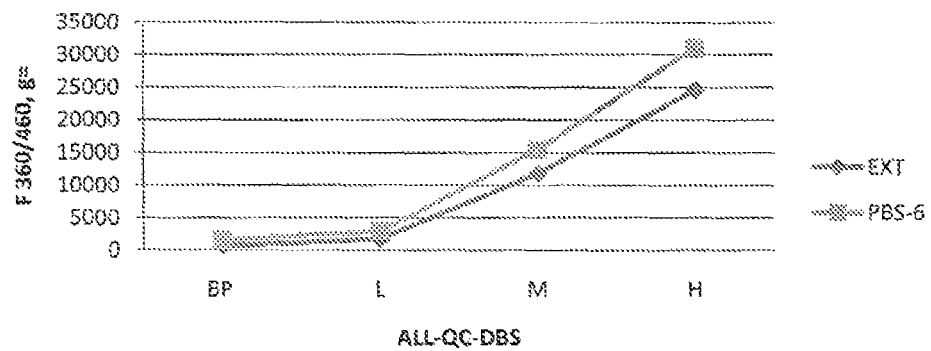

FIGS. 11A and 11B show plots 1100 and 1150, which are examples of plots of idurondate-2-sulfatase (Hunter) and α-L-iduronidase (Hurler) enzyme activities, respectively, in DBS extracts prepared on-bench using either water, 0.1% Tween® 20 (EXT) or PBS pH 6.0, 0.1% (w/v) Tween® 20 and an enzyme concentration step using ConA beads. Enzymatic assays were performed in 0.1M Acetate pH 5 (Hunter assay) and 0.04 M Acetate pH 3.5 (Hurler assay). The data associated with FIG. 11A is shown in Table 10. The data associated with FIG. 11B is shown in Table 11. Referring to FIG. 11A and Table 10, the data show idurondate-2-sulfatase (Hunter) enzyme activity in DBS extracts prepared in PBS pH 6.0, 0.1% (w/v) Tween® 20 and concentrated using a ConA bead binding step prior to analysis in 0.1M Acetate pH 5 is substantially the same as enzyme activity in DBS extracts prepared in water, 0.1% Tween® 20 (EXT). Referring to FIG. 11B and Table 11, the data show α-L-iduronidase (Hurler) enzyme activity in DBS extracts prepared in PBS pH 6.0, 0.1% (w/v) Tween® 20 and concentrated using a ConA bead binding step prior to analysis in 0.04 M Acetate pH 3.5 is higher than enzyme activity in DBS extracts prepared in water, 0.1% Tween® 20 (EXT).

TABLE 10

Effect of DBS extraction buffer composition on ConA bead binding in Hunter assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 1376 | 1699 | 9188 | 14550 | 1608 | 2118 | 8817 | 16119 |

TABLE 8

Effect of DBS extraction buffer composition on Hunter assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 359 | 486 | 2140 | 3702 | 153 | 135 | 128 | 125 |
| 351 | 479 | 2258 | 3688 | 150 | 135 | 130 | 128 |
| Ave*: 355 | Ave: 483 | Ave: 2199 | Ave: 3695 | Ave: 152 | Ave: 135 | Ave: 129 | Ave: 127 |

*Ave = average

TABLE 9

Effect of DBS extraction buffer composition on Hurler assay

| Water, 0.1% Tween ® 20 (EXT) | | | | PBS pH 6.0, 0.1% (w/v) Tween ® 20 | | | |
| --- | --- | --- | --- | --- | --- | --- | --- |
| QC-BP | QC-Low | QC-Med | QC-H | QC-BP | QC-Low | QC-Med | QC-H |
| 247 | 337 | 1297 | 2476 | 338 | 566 | 2469 | 4155 |
| 253 | 330 | 1311 | 2491 | 339 | 568 | 2436 | 4105 |
| Ave*: 250 | Ave: 334 | Ave: 1304 | Ave: 2484 | Ave: 339 | Ave: 567 | Ave: 2453 | Ave: 4130 |

*Ave = average

TABLE 11

Effect of DBS extraction buffer composition on ConA bead binding in Hurler assay

| Water, 0.1% Tween ® 20 (EXT) | | | | PBS pH 6.0, 0.1% (w/v) Tween ® 20 | | | |
|---|---|---|---|---|---|---|---|
| QC-BP | QC-Low | QC-Med | QC-H | QC-BP | QC-Low | QC-Med | QC-H |
| 640 | 1734 | 11814 | 24529 | 1654 | 3007 | 15528 | 31107 |

Figure 12A:
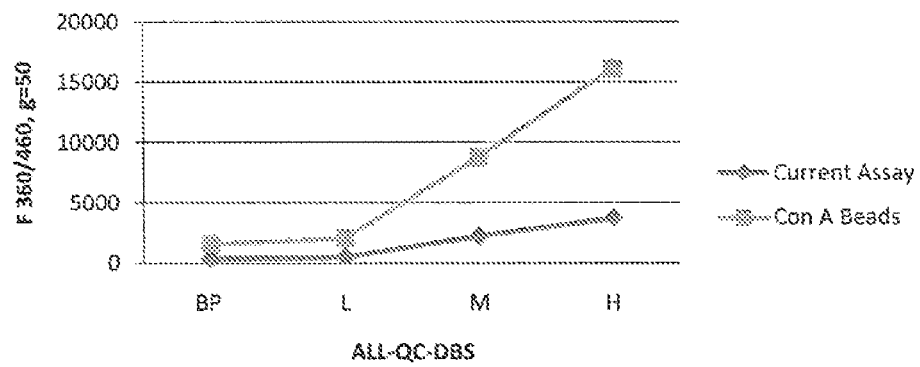
FIGS. 12A and 12B show examples of plots of idurondate-2-sulfatase (Hunter) and α-L-iduronidase (Hurler) enzyme activities, respectively, in DBS extracts prepared on-bench with or without an enzyme concentration step using ConA beads.
Figure 12B:
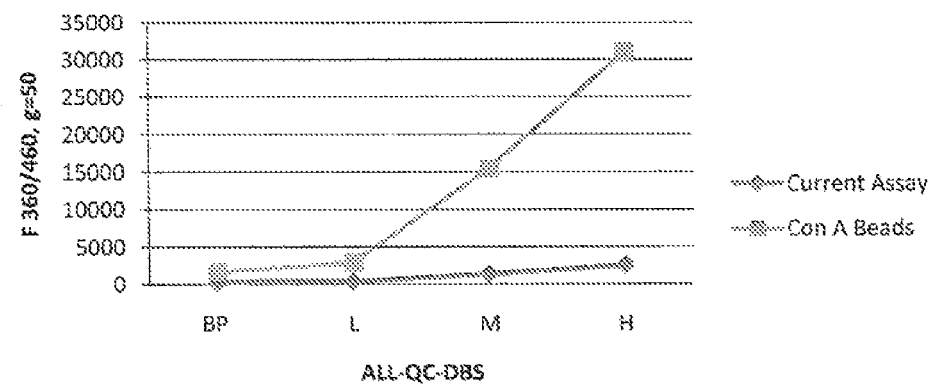

FIGS. 12A and 12B show plots 1200 and 1250, which are examples of plots of idurondate-2-sulfatase (Hunter) and α-L-iduronidase (Hurler) enzyme activities, respectively, in DBS extracts prepared on-bench with or without an enzyme concentration step using ConA beads. In this example, DBS extracts were prepared using PBS pH 6.0, 0.1% (w/v) Tween® 20. The data show increased idurondate-2-sulfatase (Hunter) and α-L-iduronidase (Hurler) enzyme activities enzyme activity in assays performed using a ConA bead binding concentration step.

7.2 Assay Methods

Digital microfluidic NBS enzyme tests are performed in aqueous droplets within an oil filled gap of the droplet actuator. Samples and assay reagents are manipulated as discrete droplets upon an electrode array (digital electrowetting). Sample droplets are blood or blood-derived samples, such as plasma, serum, tissue, cell fractions, and treated, fractionated, concentrated and/or diluted forms of the foregoing. Other biological fluids may be used as samples. Nonlimiting examples of biological fluids include tears, semen, urine, saliva, amniotic liquid, and cerebrospinal fluid. Biological fluids, e.g., DBS extracts, may be enriched and concentrated prior to performing one or more NBS assays. In one embodiment, samples for newborn testing may be prepared on-bench using magnetically responsive ConA beads to concentrate N-glycosylated proteins. The concentrated sample may be subsequently loaded onto a fluid reservoir of a droplet actuator. In another embodiment, samples for newborn testing may be concentrated and collected using ConA magnetically responsive beads on a fluid reservoir of a droplet actuator. Concentrated samples may be dispensed into one or more subsamples. In some cases, the subsamples are unit-sized subsamples. The subsamples may be in contact with or surrounded with one or more filler fluids. The samples may be analyzed using digital microfluidic protocols for one or more NBS assays.

In one example, enzymatic indicators of lysosomal storage diseases (LSDs) can be identified using droplet based assays on a droplet actuator. In one embodiment, assays of the appropriate glycosidase activity may be used to detect altered activity of a particular glycosidase, which may be an indicator of a particular lysosomal storage disease. Examples of enzyme deficiencies and LSDs include, but are not limited to, the following: a deficiency in iduronate-2-sulfae sulphatase is a diagnostic indicator of Hunter disease; a deficiency in acid β-D-glucosidase or chitotriosidase is a diagnostic indicator of Gaucher disease; a deficiency in acid sphingomyelinase or chitotriosidase is a diagnostic indicator of Niemann-Pick disease; a deficiency in α-glucosidase activity is a diagnostic indicator of Pompe disease; a deficiency in α-galactosidase activity is a diagnostic indicator of Fabry disease; a deficiency in α-L-iduronidase is a diagnostic indicator of Hurler disease; a deficiency in heparan sulfate sulfamidase is a diagnostic indicator of Sanfilippo A (MPS IIIA); a deficiency in alpha-N-acetylglucosaminidase is a diagnostic indicator of Sanfilippo B (MPS IIIB); a deficiency in arylsulfatase A is a diagnostic indicator of metachromatic leukodystrophy; and a deficiency in galactocerebrosidase (galactosylceramide beta-galactosidase) is a diagnostic indicator of Krabbe disease. Multiple diseases and/or multiple samples can be tested simultaneously on a single droplet actuator. In order to increase the sensitivity of an assay, magnetically responsive ConA beads may be used to concentrate N-glycosylated enzymes prior performing the assay.

Assay reagents for testing for lysosomal storage disorders (e.g., LSDs) on a droplet actuator may include any one or more of the following: reaction buffer, 4-MU enzyme substrate, supplemented secondary enzyme, assay-specific inhibitor, and stop buffer (e.g., 0.2M Sodium bicarbonate pH 10.0 with 0.01% Tween® 20). Examples of 4-MU substrates include, but are not limited to, 4-Methylumbelliferyl-α-L-Iduronide-2-Sulfate (4-MU-aIdoA-2S), Hunter substrate; 4-Methylumbelliferyl α-D-Galactopyranoside (4-MU-α Gal), Fabry substrate; 4-MU-α-D-glucopyranoside (4-MU-α-Gluc), Pompe substrate; 4-Methyumbelliferyl-β-D-Glucopyranoside (4-MU-β-Gluc), Gaucher substrate; 4-Methylumbelliferyl-α-L-Iduronide Sodium Salt (4-MU-α-Idu), Hurler substrate; 4-Trifluoromethylumbelliferylchitroside, Gaucher and Niemann-Pick substrate; 4-Methylumbelliferyl-β-Galactose (4-MU-β-Galactose), Morquio B substrate; 4-Methylumbelliferyl-α-N-Sulpho-D-Glucosaminide (MU-αGlcNS), Sanfilippo A (MPS IIIA) substrate; 4-Methylumbelliferyl-α-D-N-Acetylglucosamine, Sanfilippo B (MPS IIIB); 3-O-Sulfate-β-D-Galactosyl-4-Methylumbelliferyl), metachromatic leukodystrophy (MLD) substrate; and 6-hexadecanoylamino-4-methylumbelliferyl-β-D-galactoside (HMU-βGal), Krabbe substrate.

In one embodiment, the invention provides sample preparation protocols in which magnetically responsive ConA beads are used to enrich and concentrate a sample on a droplet actuator prior to performing one or more NBS assays (e.g., enzymatic assays for LSDs). In one example, a quantity (e.g., about 1 to about 20 μL, preferably about 10 μL) of magnetically responsive ConA beads may be added to a large sample volume (e.g., about 100 to about 200 μL), prior to loading the sample onto an off-actuator sample reservoir on the droplet actuator cartridge. The large volume sample may then be processed on-actuator using a bead concentration protocol into a 100 to 1320 nL droplet. In another example, a series of sample droplets (e.g., 100 to 660 nL sample droplets) may be sequentially incubated in an on-actuator sample reservoir with a single reagent droplet that contains quantity (e.g., about 1 to about 10 μL) of magnetically responsive ConA beads. Concentrated samples may be dispensed into one or more subsamples. A droplet comprising assay reagents is dispensed and merged using droplet operations with a concentrated sample droplet in a droplet operations gap or on a droplet operations surface. The combined reaction droplet is split using droplet operations into 2 reaction droplets. One reaction droplet is combined using droplet operations with a stop buffer droplet. Fluorescence of the combined droplet is measured (t=0 h). The second reaction droplet is incubated for a predetermined time and then the reaction droplet is combined with a stop buffer droplet. End point fluorescence is measured (t=END h). In this example, a single sample droplet is dispensed and analyzed. However, any number of sample droplets may be dispensed and analyzed.

7.3 Preparation of NBS Quality Control Blood Pools and DBS Samples

The invention provides methods for the preparation of whole-blood pools for use in the production of dried blood spot (DBS) quality control (QC) materials for use in newborn testing (e.g., testing for lysosomal storage disorders; LSDs).

The methods of the invention include the use of general laboratory safety precautions. For example, safety glasses, protective gloves (e.g., rubber gloves), and a laboratory coat are worn when handling all blood products. All biological specimens are disposed of in a biohazard autoclave bag and processed for disposal and hazardous waste. Liquid waste may, for example, be treated with bleach.

The methods of the invention also include the use of standard specimen collection, storage, and handling procedures. For example, an anticoagulant such as heparin or CPDA is used during specimen collection. All blood received is immediately unpacked and stored at 4° C. to 6° C. until use. The blood is used as close to the received date as possible. Any blood that is hemolysed upon receipt is not used for preparing whole blood pools. Serum (e.g., frozen charcoal-stripped human serum) is immediately unpacked and stored at –20° C. until use.

7.3.1 Heat Treatment of Serum for QC-DBS Preparation

Figure 19:
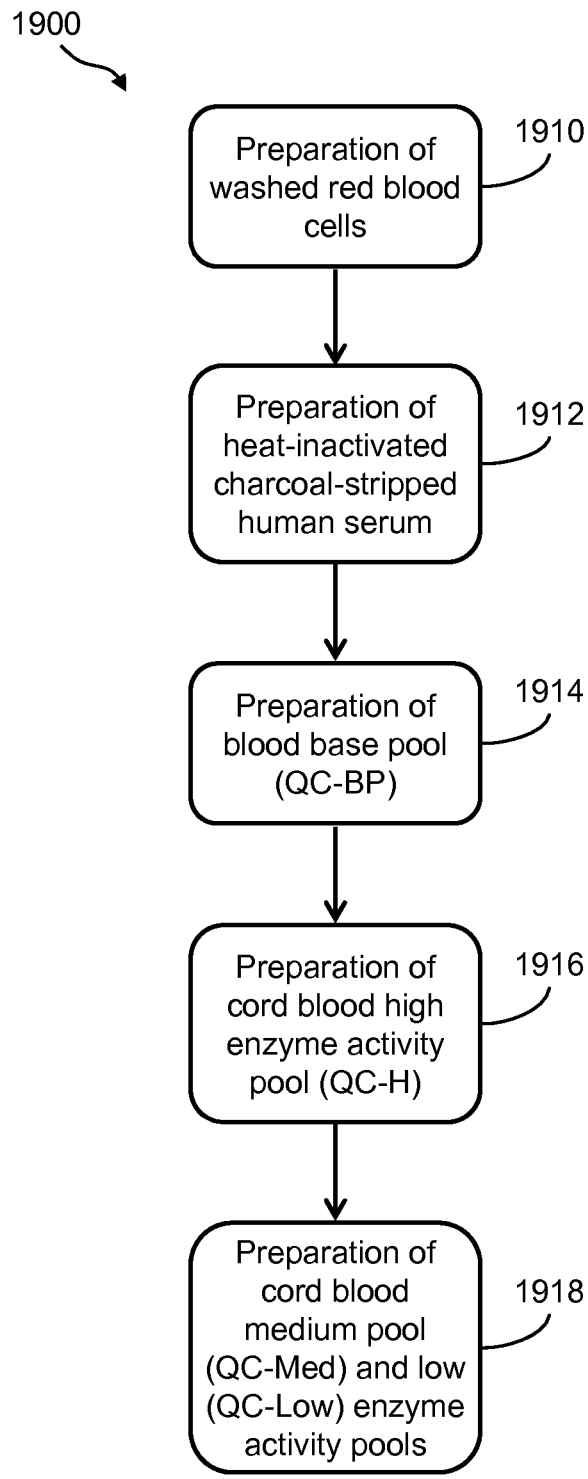
FIG. 19 shows a flow diagram of a high level overview of an example of a whole-blood pool preparation protocol for use in the production of dried blood spot (DBS) quality control (QC) materials for use in newborn testing (e.g., testing for LSDs)

Heat-inactivated serum is used for preparation of blood base pool as described in reference to FIG. 19. Heat inactivation is performed to substantially reduce enzymatic activity that may be present in the serum and interfere with NBS assays (e.g., LSDs assays). For example, idurondate-2-sulfatase (Hunter) and acid sphingomyelinase (Niemann Pick) activities are very prevalent in serum. To evaluate the effect of heat treatment on LSD enzyme activity present in serum, a volume of serum (Sera-Con II) was heat treated and on-bench assays for Fabry, Gaucher, Hunter, Niemann Pick and Pompe enzymatic activity present in the serum were performed at various time points. The on-bench assay included the following steps: A 1 L bottle of frozen Sera-Con II serum was stored overnight at 4° C. A water bath was set at 55° C. and allowed to equilibrate. The bottle of serum was soaked in a container under running cold water to complete thawing. The thawed bottle of serum was placed in the 55° C. water bath and the temperature of the serum recorded every 15 minutes until the serum reached 55° C. A 1 mL aliquot of serum was removed at 0, 0.5, 1, 2, 3, and 4 hour time points. Serum from each time point was assayed in triplicate for Fabry, Gaucher, Hunter, Niemann Pick, and Pompe enzyme activity present in the serum using on-bench microtiter plate protocols and appropriate enzyme substrates. A single row on each assay plate included substrate only and was used as an assay control for non-enzymatic hydrolysis (NEH). The reactions were incubated at 37° C. for 20 hrs (overnight). At the end of the incubation period, 50 µL of stop buffer was added to all samples and the fluorescence determined 4-MU and HMU standard curves were run to calculate enzymatic activity. NEH sample values were subtracted from raw values.

Figure 13:
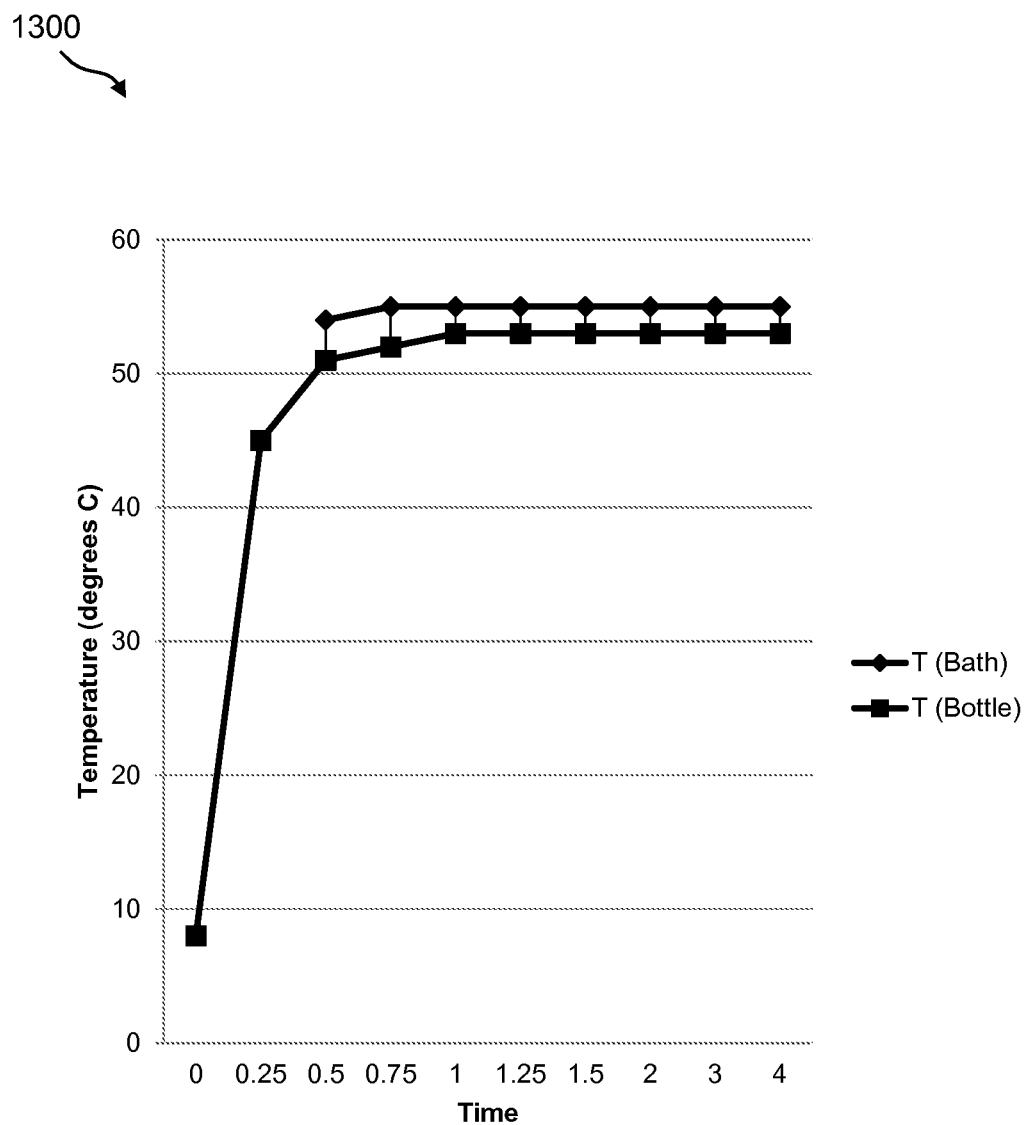
FIG. 13 shows an example of a plot of a temperature profile during heat inactivation of serum.

FIG. 13 shows a plot 1300, which is an example of a plot of a temperature profile during heat inactivation of serum. A water bath was set at 55° C. and allowed to equilibrate. A thawed bottle of serum was placed in the 55° C. water bath and the temperature of the serum recorded every 15 minutes until the serum reached 55° C. The data show that the temperature of the serum did not stabilize until after about 1 hour incubation in the water bath. The data also shows that the bottle (Nalgene bottle) insulated the serum from the water bath temperature by about 2° C. throughout the experiment. To account for insulation by the serum bottle, the temperature of the water bath may be adjusted to about 57° C. or about 58° C.

Figure 14:
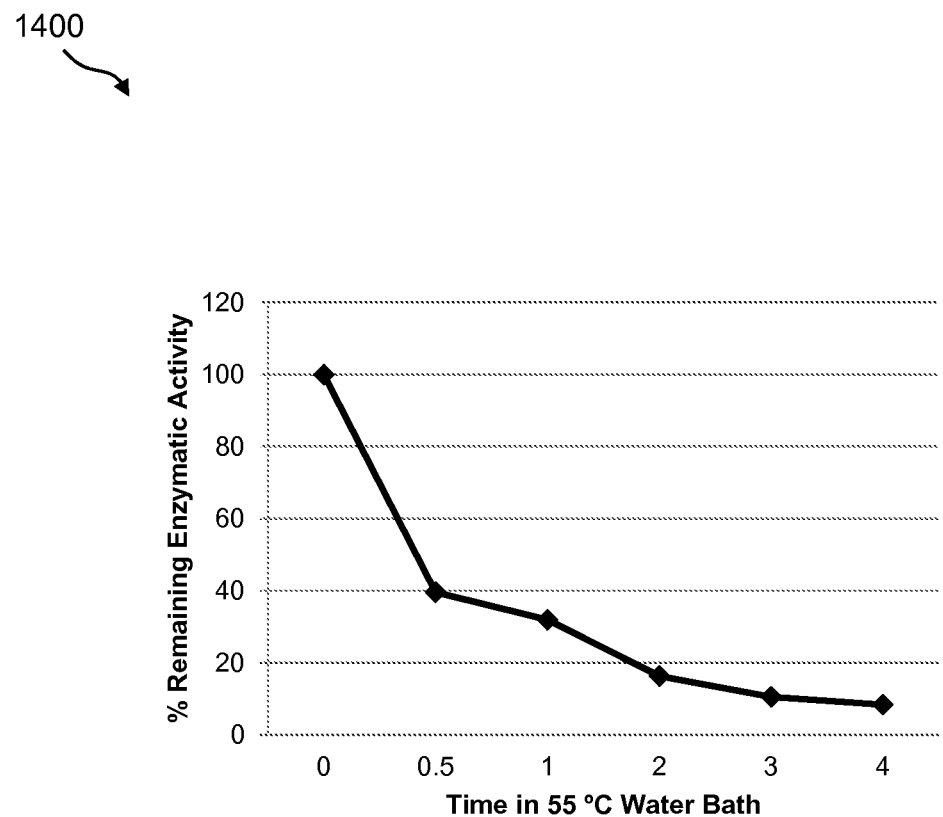
FIG. 14 shows an example of a plot of α-galactosidase activity (Fabry) in heat treated serum.

FIG. 14 shows a plot 1400, which is an example of a plot of α-galactosidase activity (Fabry) in heat treated serum. The enzyme substrate for α-galactosidase activity was 4-methylumbelliferyl α-D-glactopyranoside. The stop buffer was 0.2 M Sodium bicarbonate pH 10.1 with 0.01% (w/v) Tween 20. 4-MU fluorescence was read at 360/460 excitation/emission. The data show after 1 hour incubation the remaining α-galactosidase activity in the serum was about 30%. After 4 hours incubation, the remaining α-galactosidase activity in the serum was about 10%.

Figure 15:
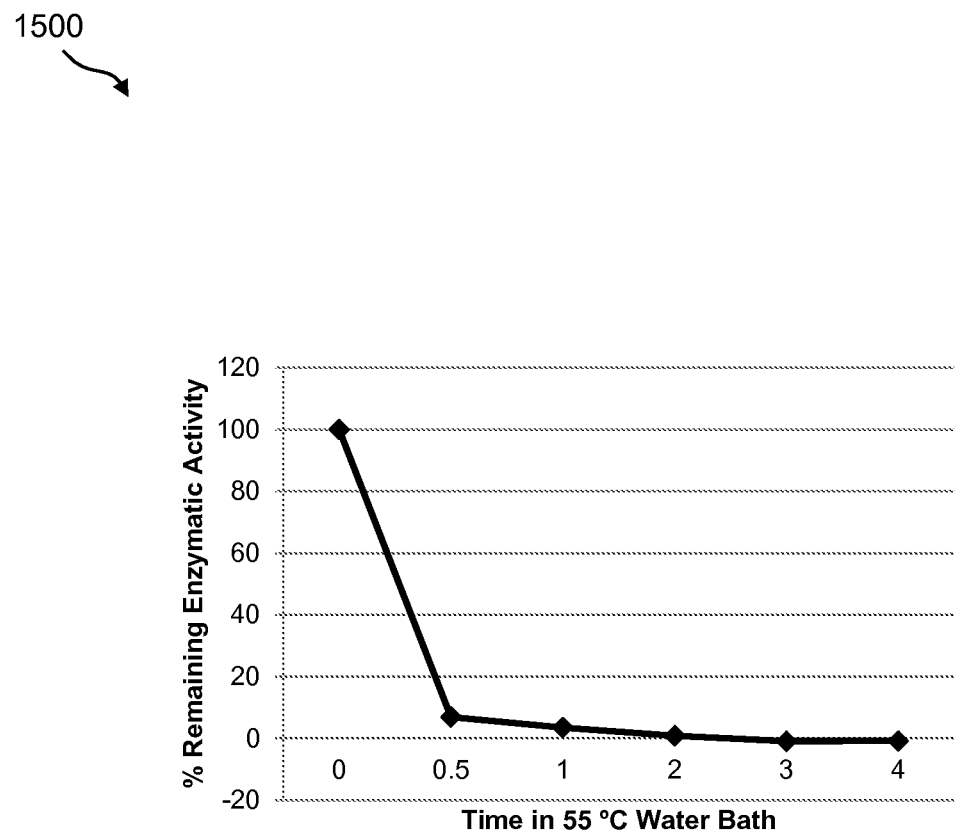
FIG. 15 shows an example of a plot of β-glucosidase activity (Gaucher) in heat treated serum.

FIG. 15 shows a plot 1500, which is an example of a plot of β-glucosidase activity (Gaucher) in heat treated serum. The enzyme substrate for β-glucosidase activity was 4-methylumbelliferyl-β-D-glucopyranoside. The stop buffer was 0.2 M Sodium bicarbonate pH 10.1 with 0.01% (w/v) Tween 20. 4-MU fluorescence was read at 360/460 excitation/emission. The data show after 1 hour incubation the remaining β-glucosidase activity in the serum was substantially reduced (less than about 5%).

Figure 16:
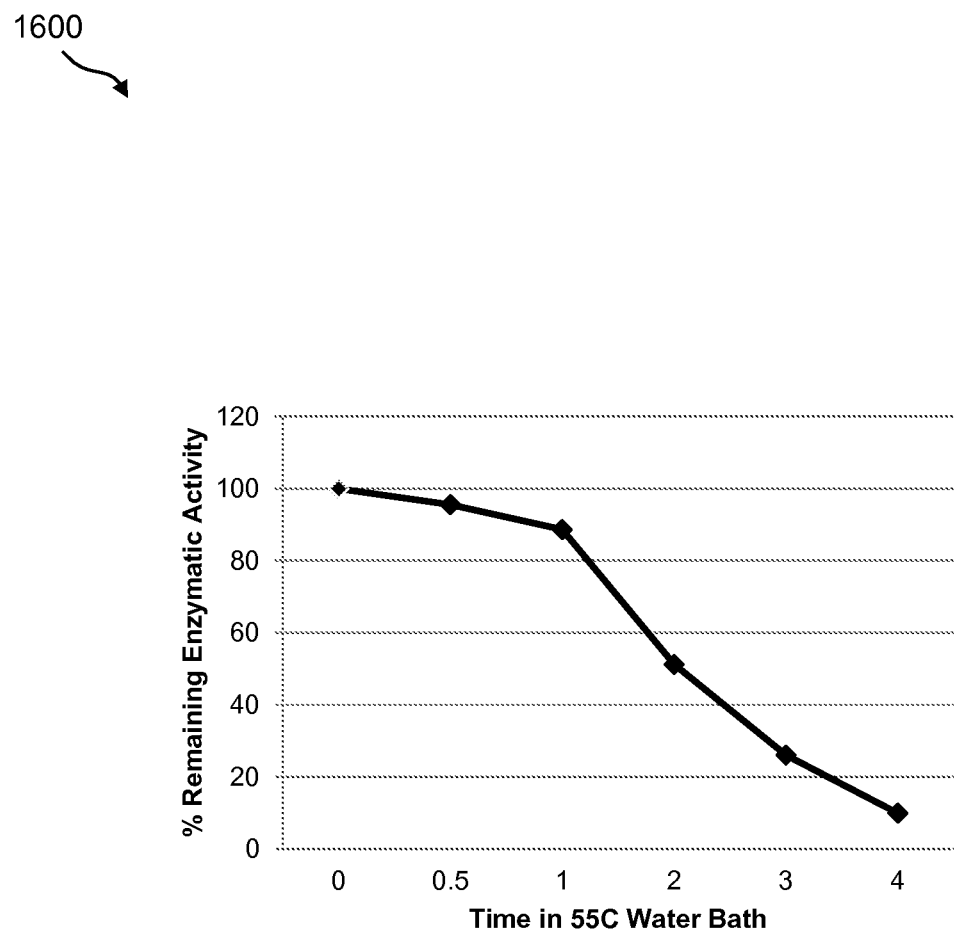
FIG. 16 shows an example of a plot of idurondate-2-sulfatase activity (Hunter) in heat treated serum.

FIG. 16 shows a plot 1600, which is an example of a plot of idurondate-2-sulfatase activity (Hunter) in heat treated serum. The enzyme substrate for idurondate-2-sulfatase activity was 4-methylumbelliferyl α-L-iduronic acid-2-sulfate. The stop buffer was 0.2 M Sodium bicarbonate pH 10.1 with 0.01% (w/v) Tween 20. 4-MU fluorescence was read at 360/460 excitation/emission. The data show after 1 hour incubation the remaining idurondate-2-sulfatase activity in the serum was about 90%. After 4 hours incubation, the remaining idurondate-2-sulfatase activity in the serum was about 10%. A longer heat treatment time, e.g., about 4 hours or longer, may be selected to substantially eliminate (reduce) idurondate-2-sulfatase activity in serum.

Figure 17:
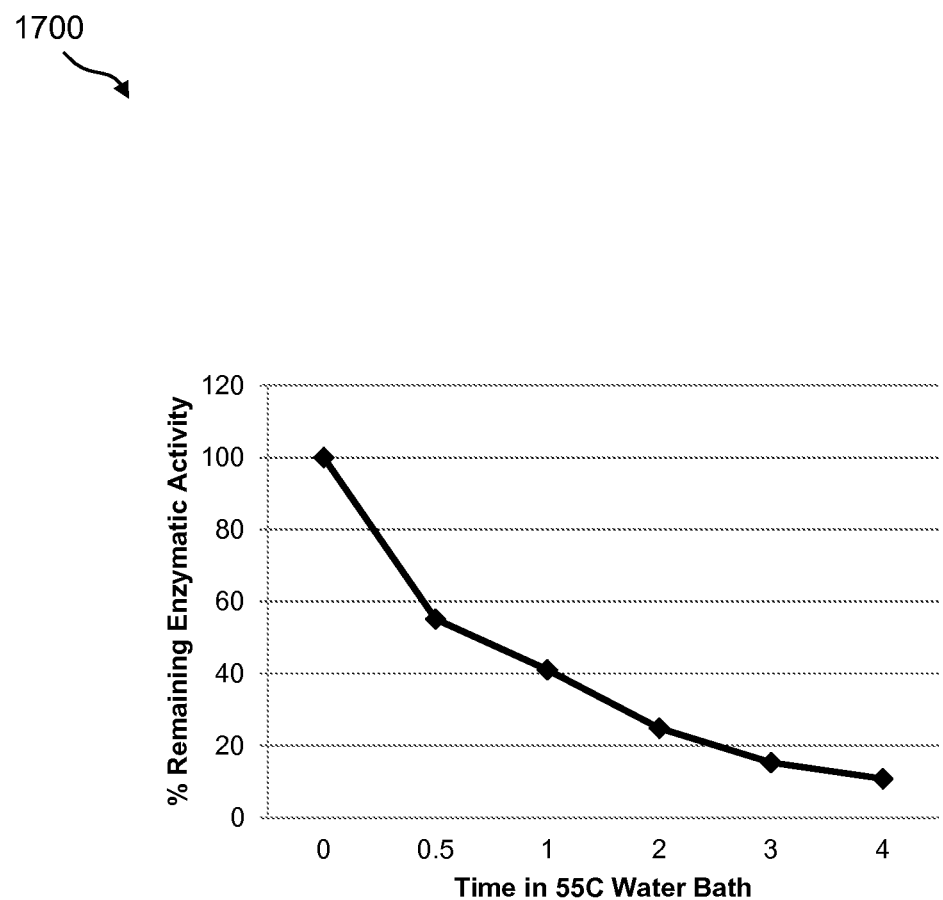
FIG. 17 shows an example of a plot of acid sphingomyelinase activity (Niemann Pick) in heat treated serum.

FIG. 17 shows a plot 1700, which is an example of a plot of acid sphingomyelinase activity (Niemann Pick) in heat treated serum. The enzyme substrate for acid sphingomyelinase activity was 6-hexadecanoylamido-4-methylumbelliferyl-phosphorylcholine. The stop buffer was 0.2 M Sodium bicarbonate pH 10.1 with 0.25% (w/v) TritonX-100. HMU fluorescence was read at 400/460 excitation/emission. The data show after 1 hour incubation the remaining acid sphingomyelinase activity in the serum was about 40%. After 4 hours incubation, the remaining acid sphingomyelinase activity in the serum was about 10%. A longer heat treatment time, e.g., about 4 hours or longer, may be selected to substantially eliminate (reduce) acid sphingomyelinase activity in serum.

Figure 18:
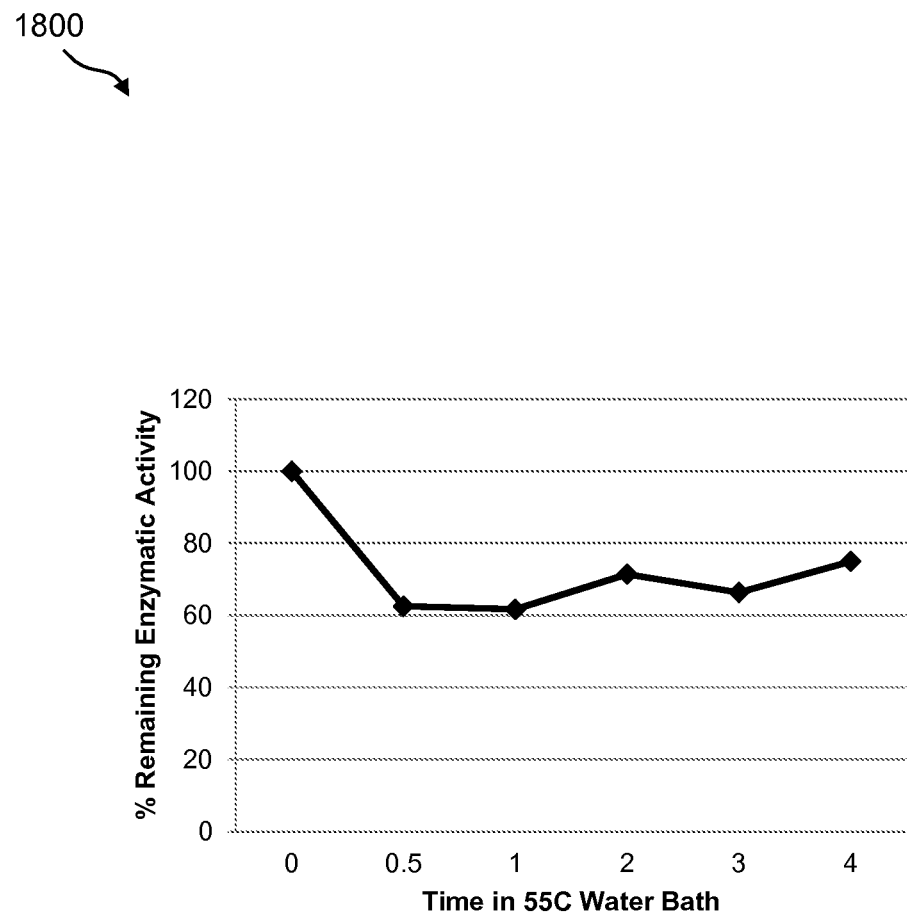
FIG. 18 shows an example of a plot of acidic α-glucosidase activity (Pompe) in heat treated serum.

FIG. 18 shows a plot 1800, which is an example of a plot of acidic α-glucosidase activity (Pompe) in heat treated serum. The enzyme substrate for acidic α-glucosidase activity was 4-methylumbelliferyl α-D-glucopyranoside. The stop buffer was 0.2 M Sodium bicarbonate pH 10.1 with 0.01% (w/v) Tween 20. 4-MU fluorescence was read at 360/460 excitation/emission. The data show after 4 hour incubation the remaining acidic α-glucosidase activity in the serum was about 40%.

Non-enzymatic hydrolysis (NEH) of assay substrates is shown in Table 12.

TABLE 12

| Non-enzymatic hydrolysis of substrates | |
|---|---|
| Assay | % Increase NEH |
| Pompe | 12 |
| Fabry | –5 |
| Gaucher | 7 |
| Hunter | 55 |
| Niemann Pick | 23 |

7.3.2 NBS QC Blood Pools

FIG. 19 shows a flow diagram of a high level overview of an example of a whole-blood pool preparation protocol 1900 for use in the production of dried blood spot (DBS) quality control (QC) materials for use in newborn testing (e.g., testing for LSDs). Protocol 1900 may include, but is not limited to, the following steps.

At step 1910, fresh, packed human red blood cells (i.e., O$^+$ type) are washed for preparation of a QC blood base pool (QC-BP). Blood from several donors of the same blood type (i.e., type) may be combined for preparation of a QC-BP. The volume and hematocrit of the washed red blood cell pool is determined. The hematocrit should be about 95% or higher.

At step 1912, heat-inactivated charcoal-stripped human serum is prepared. Frozen aliquots of charcoal-stripped human serum are thawed overnight at 4° C. to 6° C. and subsequently heat-inactivated in a 55° C. water bath for about 4 hours.

At step 1914, the hematocrit of the washed red blood cell pool is adjusted with the heat-inactivated human serum to form the blood base pool (QC-BP). The hematocrit of a QC-BP is about 50%±1%.

At step 1916, unprocessed cord blood units (i.e., O$^+$ type) are combined and the hematocrit of the pool determined. The cord blood pool is centrifuged and the hematocrit of the cord blood pool (QC-H) is adjusted to about 50%±1% by removal/addition of supernatant.

At step 1918, aliquots of QC-BP and QC-H are combined to form a medium enzyme activity pool (QC-Med) and a low enzyme activity pool (QC-Low). QC-Med is composed of 50% QC-H and 50% QC-BP. QC-Low is composed of 5% QC-H and 95% QC-BP.

Referring again to step 1910 of protocol 1900, an example of a protocol for preparation of washed red blood cells includes the following steps:
1. Set up vacuum system under a chemical hood using two side arm flasks (e.g., 1000 mL Erlenmeyer flasks). Attach the rubber hose from one flask side arm directly to the filter that is attached to the vacuum connection under the hood. Place appropriately sized rubber stopper with glass tubing on top of flask. Attach rubber tubing from side arm of second flask onto the glass tubing from the rubber stopper of first flask. Attach a glass pipette tip to the rubber hose coming from the side arm of the second flask;
2. Cool a refrigerated large volume centrifuge (e.g., Beckman Coulter centrifuge) to about 6-8° C.;
3. Fill centrifuge bottles (e.g., 250 mL or 1 L Nalgene Beckman centrifuge bottles) about half way with packed red blood cells;
4. Add equal volumes of saline (sodium chloride 0.9% injection USP) to the cells in the centrifuge bottles. Gently invert about 5-10 times to ensure complete mixture of the red cells with saline taking care to preserve integrity of red cells;
5. Centrifuge red cells and saline mixture for 10 minutes at 3200 rpm at about 6-8° C. If necessary adjust the brake setting on the centrifuge to low or off so that the cells do not remix at the end of the centrifuge cycle;
6. Carefully remove bottles from centrifuge without disturbing the cell layers and transfer the bottles to the chemical hood where the vacuum system has been set up;
7. Using the vacuum system, aspirate the majority of the saline supernatant and buffy coat layer from the red cells. Leave a small amount of the supernatant over the red cells to retain as much red cell volume as possible. Each time the waste flask fills, empty its contents into the sink and pour bleach in the sink afterwards;
8. Repeat steps 4, 5, 6, and 7;
9. After the second wash has been aspirated, add equal volume of saline to the red cells and gently invert 5-10 times to ensure adequate mixing. This is the final wash. Centrifuge the final wash at 4000 rpm for 15 minutes;
10. Carefully remove all of the supernatant using the vacuum system;
11. Place a clean 1000 mL beaker on a magnetic stirring table. Place a stirring bar in the beaker;
12. Pour the red cells from the centrifuge bottles into a 250 mL graduated cylinder (or a 500 mL graduated cylinder depending on the amount of blood processed) to measure the amount of washed red cells. The volume of red cells recovered will be used to calculate the amount of heat-inactivated serum required for preparation of a blood base pool as described in reference to Step 3 of FIG. 19. Pour the cells from the graduated cylinder into the 1000 mL beaker and stir gently with the aid of an automatic stirrer for 10-15 minutes;
13. Measure the hematocrit (hct):
    i. Fill four microcapillary (microhematocrit) tubes with blood from the beaker and stopper the end using a clay sealer. Place the four stoppered microcapillary tubes into a microcentrifuge (e.g., IEC Microhematocrit centrifuge) and centrifuge for 4 minutes;
    ii. Place the centrifuged microcapillary tubes in the groove of the plastic indicator on a microcapillary tube reader such that the bottom of the column of the red cells coincides with the black line on the plastic indicator;
    iii. Rotate the bottom plate so that the 100 percent line is directly beneath the red line on the plastic indicator. Hold the bottom plate in this position. Using the finger hole, rotate the top plate so that the spiral line intersects the microcapillary tube at the plasma-air interface;
    iv. Rotate both discs together until this spiral line intersects the microcapillary tube at the red cell/white cell interface;
    v. Red cell volume in percent is read from the point on the scale directly beneath the red line of the plastic indicator;
    vi. Repeat this measurement for all four tubes; and
    vii. Take the average of the four individual hct measurements. The average hct measurement will be used to calculate the amount of heat-inactivated serum required for preparation of a blood base pool as described in the example protocol of Step 3 of FIG. 19. The hematocrit should be 95% or higher. If the hematocrit is <95%, centrifuge the cells again and remove more saline supernatant. Measure the cell volume and hematocrit again.

At this point, the washed red cells are ready for preparation of blood base pool. Alternatively, the washed red cells may be stored in the refrigerator overnight prior to preparation of blood base pool.

Referring again to step 1912 of protocol 1900, an example of a protocol for preparation of heat-inactivated, charcoal stripped human serum includes the following steps:
1. Remove the charcoal stripped human serum from the freezer and store it at 4° C. This step is performed the day before the heat inactivation is performed;
2. For heat-inactivation of the serum, turn on a water bath and set the temperature to 55° C. Allow the temperature of the water bath to reach 55° C. before proceeding;

3. Remove the charcoal stripped human serum from the refrigerator. If it is not completely thawed, soak the bottle in a container under running cold water until it is thawed;
4. Put the bottle of thawed charcoal stripped serum into the water bath and observe the temperature of the water bath;
5. When the water bath returns to the target temperature (55° C.), set a timer for 1 hour;
6. Gently invert the serum bottle 3 times during the 1 hour incubation;
7. Repeat steps 5 and 6 three times for a total of 4 hours for heat-inactivation;
8. When the incubation is complete, cool down the serum under running cold water; and
9. Filter the heat-inactivated serum using cheese cloth.

Referring again to step 1914 of protocol 1900, an example of a protocol for preparation of a blood base pool (QC-BP) includes the following steps:
1. The measured red cell volume and average hematocrit of the washed red cell pool (as described in the example protocol of step 1910 of protocol 1900) are used to determine the amount of heat-inactivated charcoal stripped human serum to add to the washed red cells to adjust the hematocrit level to 50% as follows: (Volume of recovered red cells)(Current hct)=(Desired hct)(Total amount of reconstituted blood); Amount serum needed= (total amount of reconstituted blood)–(volume of recovered RBC);
2. Measure the calculated amount of heat-inactivated, charcoal stripped human serum using a graduated cylinder. Add the serum to the beaker containing the washed red cells;
3. Using a magnetic stirrer, stir for 5-10 minutes to ensure adequate mixing of the serum and red cells; and
4. Measure the hematocrit (hct) as described in the example protocol of Step 1 of FIG. 19. The average hematocrit content of four samples should be about 50%±1%. If the end hematocrit is too high, calculate and add an appropriate amount of prepared serum to adjust. If the end hematocrit is too low, allow the red cells to settle and remove some of the serum from the mixture. Repeat the hematocrit measurement.

Referring again to step 1916 of protocol 1900, an example of a protocol for preparation of a cord blood high enzyme activity pool includes the following steps:
1. Place a clean beaker on a magnetic stir plate. Place a magnetic stirring bar in the beaker;
2. Pour the cord blood units from the collection bags into the beaker and stir for 5-10 minutes;
3. Measure the hematocrit level of the pooled cord blood as described in the example protocol of step 1910 of protocol 1900. Cord blood hematocrit is typically about 33%;
4. Transfer the cord blood to a 250 mL graduated cylinder (or a 500 mL graduated cylinder depending n the volume of cord blood to be processed) and measure the amount of cord blood;
5. The measured cord blood volume (step 4) and average hematocrit value (step 3) are used to calculate the amount of cord blood supernatant that needs to be removed to adjust the hematocrit to 50% as follows: (Volume of current cord blood)(Current hct)=(Desired hct)(Calculated amount of cord blood); Amount supernatant removed=(Volume of current blood)–(Calculated amount of cord blood);
6. Pour the cord blood from the graduated cylinder into a centrifuge bottle (e.g., Nalgene Beckman centrifuge bottle) and centrifuge the cord blood at 6-8° C. for 10 minutes at 2500 rpm;
7. Remove the calculated amount of supernatant from the centrifuged cord blood. Reserve the removed supernatant for further adjustments as needed;
8. Pour the remaining cord blood from the centrifuge bottle into the beaker and stir using an automatic stirrer for 5-10 minutes; and
9. Measure the hematocrit (hct) as described in the example protocol of step 1910 of protocol 1900. The average hematocrit content of four samples should be about 50%±1%. If the end hematocrit is too high, calculate and add an appropriate of the reserved supernatant to adjust. If the end hematocrit is too low, allow the cells to settle and remove some of the supernatant from the mixture. Repeat the hematocrit measurement.

Referring again to step 1918 of protocol 1900, an example of a protocol for preparation of a cord blood medium pool and low enzyme activity pool includes the following steps:
1. Record the volume of blood base pool and cord blood high enzyme activity pool prepared as described in the example protocols of steps 1914 and 1916 of protocol 1900, respectively. The amount of blood base pool should be at least 1.7 times the amount of cord blood high enzyme activity pool;
2. Equal volumes (i.e., 50:50 mixture) of blood base pool (QC-BP) and cord blood pool (QC-H) will be used to form a cord blood medium enzyme activity pool (QC-Med);
3. To make a cord blood low enzyme activity pool (QC-Low), 95% blood base pool (QC-BP) and 5% cord blood pool (QC-H) will be combined;
4. Use the following calculation to estimate the size of each QC pool and volumes required:

Volume of individual QC pool=(amount of cord blood pool)/1.6

For example: amount of cord blood=200 mL; Volume of individual QC pool=200/1.6=125 mL
Then, QC blood base pool=125 mL
QC Low pool=(118.75 mL of base pool)+(6.25 mL of cord blood pool)=125 mL
QC Med pool=(62.5 mL of base pool)+(62.5 mL of cord blood pool)=125 mL
QC High pool=125 mL
Thus, total blood base pool needed: 125±118.75±62.5=306.25
Total cord blood pool needed: 125±6.25±62.5=193.75 mL; and
5. According to the calculations in Step 4, use a 250 mL graduated cylinders to measure and mix the base pool and cord blood high pool to make the QC-Med and QC-Low pools.

Figure 20:
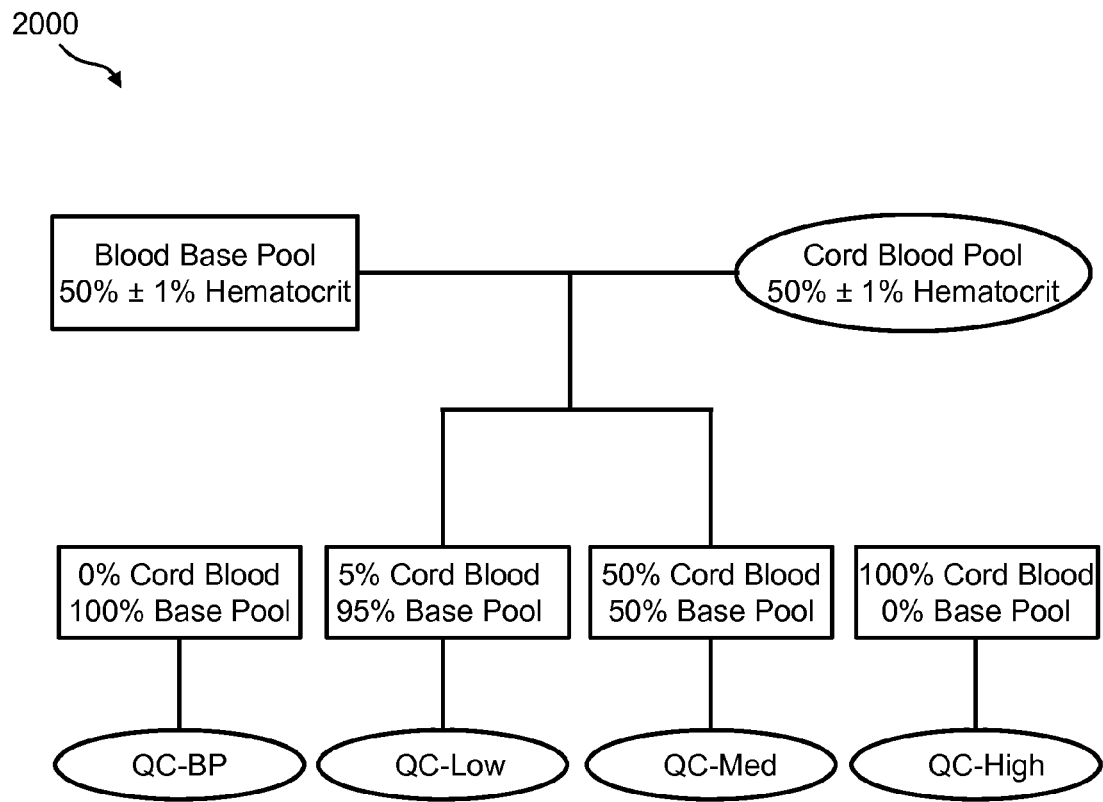
FIG. 20 shows an example of quality control blood pool compositions for use in preparation of DBS samples for newborn testing.

FIG. 20 shows a diagram 2000 of an example of quality control blood pool compositions for use in preparation of DBS samples for newborn testing. QC blood pools include a blood base pool and a cord blood pool. A QC blood base pool (QC BP) is composed of 100% blood base pool sample. The hematocrit of a blood base pool is about 50%±1%. A QC high (QC-H) pool is composed of 100% cord blood sample. The hematocrit of a cord blood pool is about 50%±1%. Aliquots of a blood base pool and a cord blood pool are combined to form a QC medium (QC-Med) enzyme activity blood pool composed of 50% cord blood and 50% base pool; and a QC-Low enzyme activity blood pool composed of 5% cord blood and 95% blood base pool.

7.3.3 QC DBS Samples

The prepared whole-blood pools may be used to produce DBS quality control materials for use in newborn testing, e.g., for lysosomal storage disorders. An example of a protocol for preparing DBS QC materials (e.g., filter paper cards) includes, but is not limited to, the following steps:

1. Obtain printed spot cards (e.g., Advanced Liquid Logic 15 Spot cards);
2. Label the cards with type of Pool, Lot Number, and Date;
3. Starting with the Blood Base Pool (BP), place 100 μL of blood on each designated spot on the card (e.g., 15 spots on the Advanced Liquid Logic 15 Spot card). Continue to spot cards until all of the prepared blood pool has been used. Place the cards on a rack and allow to dry overnight;
4. Repeat steps 2 and 3 for each blood pool (i.e., QC-H, QC-Med, and QC-Low); and
5. After drying, segregate the cards by pool and place them into sealable bags with desiccant. Label the outside of each bag and store at −80° C. (Spots are stable for up to one year if stored at −80° C.).

7.4 Reducing Contamination in NBS Assays

Unknown contaminates in a biological sample (e.g., a blood sample) used in newborn screening assays may result in false positive test results. The false positives typically occur in premature babies in the Neonatal Intensive Care Unit (NICU), and are probably attributable to certain pharmaceuticals the infants are receiving in the NICU. The false positive test results are problematic regardless of the testing methodology used (e.g., microtiter plate-based fluorescent assays, tandem mass spectrometry (MS/MS), and digital microfluidic assays).

The present invention provides methods to substantially eliminate contaminates that may inhibit enzyme activity and cause false positive readings in screening assays (e.g., NBS assays) and diagnostic tests. In various embodiments, magnetically responsive ConA beads are used to eliminate contaminants and concentrate N-glycosylated enzymes in a biological sample prior to performing a screening assay or diagnostic test.

An example of an enzyme purification process to eliminate contaminates in a biological sample (e.g., a blood sample) may include, but is not limited to, the following steps: A quantity of magnetically responsive ConA beads (e.g., SiMAG-ConA beads or streptavidin-biotin coupled ConA beads) are added to a volume of biological sample (e.g., a blood sample). After a period of time sufficient for N-glycosylated enzymes to bind to the magnetically responsive ConA beads, the beads are immobilized using a magnet. The supernatant containing unbound molecules (e.g., inhibitory contaminants) is removed and discarded to waste. The magnetically responsive ConA beads with N-glycosylated enzymes thereon are washed one or more times using a bead washing protocol to further remove unbound material, yielding a washed bead sample substantially lacking in unbound material. Purified N-glycosylated enzymes bound to magnetically responsive ConA beads are then eluted from the beads (e.g., using a competing molecule for SiMAG-ConA beads or bond cleavage for streptavidin-biotin coupled ConA beads). The magnetically responsive ConA beads are immobilized using a magnet and the eluate removed for sample analysis (e.g., NBS enzymatic assays).

In one embodiment, enzyme purification and enzymatic assays may be performed on a droplet actuator. An example of an on-actuator purification protocol includes, but is not limited to, the following steps: A sample droplet (e.g., DBS extract droplet) is combined using droplet operations with a reagent droplet that includes a quantity of magnetically responsive ConA beads to yield a sample/bead binding droplet. The sample/bead binding droplet is incubated for a sufficient period of time for N-glycosylated enzymes to bind to the magnetically responsive ConA beads. The sample/bead binding droplet is transported using droplet operations into the presence of a magnet and washed using a merge-and-split wash protocol to remove unbound material, yielding a washed bead-containing droplet substantially lacking in unbound material. The purified glycosylated enzymes are then eluted (e.g., using competing molecules or bond cleavage) from the beads. The eluted enzymes contained in the supernatant droplet surrounding the beads may then be transported away from the magnetically responsive beads for further processing on the droplet actuator, e.g., for execution of droplet based NBS assay protocols.

In another embodiment, enzyme purification may be performed on a droplet actuator and the purified sample subsequently removed from the droplet actuator for off-actuator testing. In this example, the supernatant droplet (eluate) containing purified enzyme may be transported using droplet operations to a reservoir in fluid communication with an opening in the top substrate of the droplet actuator. The supernatant droplet may be removed from the droplet actuator via openings in the top substrate of the droplet actuator. The purified sample may be analyzed using off-actuator methodologies, such as MS/MS assays and microtiter-based fluorescence screening assays.

In yet another embodiment, enzyme purification may be performed on a droplet actuator and one or more enzymatic assays performed on-actuator prior to removing the prepared sample for analysis off-actuator. In one example, an enzyme purification and enzymatic processing protocol may be used prepare a sample(s) for analysis on a mass spectrometry platform. The prepared sample droplet(s) may be transported using droplet operations to a reservoir(s) in fluid communication with openings in the top substrate of the droplet actuator. The prepared sample droplet(s) may be stamped onto the mass spectrometry platform via openings in the top substrate of the droplet actuator.

In yet another embodiment, enzyme purification may be performed off-actuator and the purified sample analyzed using off-actuator methodologies such as mass spectrometry and/or microtiter plate based assays.

In yet another embodiment, enzyme purification may be performed off-actuator and the purified sample loaded onto a reservoir in fluid communication with an opening for flowing liquid from the reservoir into the droplet operations gap of a droplet actuator. The purified sample may then be analyzed on-actuator using digital microfluidic protocols.

7.5 Systems

It will be appreciated that various aspects of the invention may be embodied as a method, system, computer readable medium, and/or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the invention may be written in an object oriented programming language such as Java, Smalltalk, C++ or the like. However, the program code for carrying out operations of the invention may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The invention may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The invention may be applied to any wireless/wireline communications network, regardless of physical componentry, physical configuration, or communications standard(s).

Certain aspects of invention are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the invention.

8 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

The invention claimed is:

1. A method of conducting an assay for measuring enzymatic modification of the substrate by a glycoprotein having enzymatic activity, the method comprising:
   (a) preparing an output sample comprising glycoproteins having enzymatic activity, comprising:
      (i) providing an input sample comprising glycoproteins having enzymatic activity;
      (ii) capturing the glycoproteins from the input sample on a solid support;
      (iii) washing the glycoproteins captured on a solid support to remove unbound portions of the input sample, wherein steps (ii) and (iii) are performed in one or more droplets in oil; and (iv) eluting glycoproteins from the solid support to yield an output sample comprising glycoproteins having enzymatic activity;

(b) adding an enzyme substrate to the output sample comprising glycoproteins having enzymatic activity; and (c) measuring enzymatic modification of the substrate.

2. The method of claim 1, wherein the substrate comprises a glycoside substrate.

3. The method of claim 1, wherein the substrate releases a detectable fluorophore upon contact with the output sample comprising glycoproteins having enzymatic activity.

4. The method of claim 1, wherein the substrate comprises a glycoside substrate which releases a fluorophore upon contact with the output sample comprising glycoproteins having enzymatic activity.

5. The method claim 1, wherein the eluting is accomplished by contacting the solid support with one or more glycomimetics.

6. The method of claim 1, wherein the eluting is accomplished by cleaving a cleavable bond between the solid support and captured glycoproteins.

7. The method claim 1, wherein the input sample is selected from the group consisting of: blood, plasma, serum, tears, saliva, and urine.

8. The method of claim 1, wherein the input sample comprises fresh blood.

9. The method of claim 1, wherein the input sample comprises reconstituted dried blood.

10. The method of claim 1, wherein the input sample consists essentially of plasma.

11. The method of claim 1, wherein the input sample comprises a human clinical sample.

12. The method of claim 1, wherein the solid support comprises concanavalin A.

13. The method of claim 1, wherein the solid support comprises a magnetically responsive bead.

14. The method of claim 1, wherein the captured glycoproteins comprise one or more enzymes.

15. The method of claim 1, wherein the captured glycoproteins comprise one or more glycosidase enzymes.

16. The method of claim 1, wherein the input sample is collected from a subject and immediately loaded onto a droplet actuator and the method is immediately performed.

* * * * *